US005786141A

United States Patent [19]
Bard et al.

[11] Patent Number: 5,786,141
[45] Date of Patent: Jul. 28, 1998

[54] ELECTROGENERATED CHEMILUMINESCENCE LABELS FOR ANALYSIS AND/OR REFERENCING

[76] Inventors: Allen J. Bard, 6202 Mountainclimb Dr., Austin, Tex. 78731; Thomas Richards, 208 Westhaven Dr., Austin, Tex. 78746; Jonathan K. Leland, 14236 Amberleigh Ter., Silver Spring, Md. 20906

[21] Appl. No.: 385,864

[22] Filed: Feb. 9, 1995

Related U.S. Application Data

[63] Continuation-in-part of Ser. No. 296,630, Aug. 26, 1994, abandoned.

[51] Int. Cl.[6] .............................. C12Q 1/68; C12Q 1/70; C12P 19/34; G01N 33/53
[52] U.S. Cl. .................................. 435/6; 435/5; 435/91.1; 435/91.2; 435/7.1; 536/26.6; 422/178.1; 436/518; 436/149; 530/388.1; 530/300
[58] Field of Search ........................... 536/26.6; 435/6, 435/5, 91.1, 91.2, 7.1, 7.2, 7.95; 436/518, 149; 530/388.1, 300; 422/178.1

[56] References Cited

U.S. PATENT DOCUMENTS

| 5,132,429 | 7/1992 | Narita et al. |       |
|-----------|--------|---------------|-------|
| 5,221,605 | 6/1993 | Bard et al.   |       |
| 5,238,808 | 8/1993 | Bard et al.   | 435/4 |
| 5,310,687 | 5/1994 | Bard et al.   |       |
| 5,324,457 | 6/1994 | Zhang et al.  |       |

OTHER PUBLICATIONS

A.W. Knight and G.M. Greenway, 119 Analyst, vol. 119: 870–890 (May 1994).
M.T. Carter and A.J. Bard, Bioconjugate Chem., vol. 4 257–263 (1990).
Hung Yyuan Cheng et al. 100:3 Journal of the American Chemical Society, 962–967 (1978).
Andrew Deputy et al., J. Phys. Chem., vol. 94: 3620–3623 (1990).
T.J. Mellinger and C.E. Keeler "Factors Influencing Spectrofluorometry of Phenothiazine Drugs", Analytical Chemistry, vol. 36: 1840–1847 (Aug. 1964).
T.J. Mellinger and C.E. Keeler, "Spectrofluorometric Identification of Phenothiazine Drugs", C.E. Anal. Chem., vol. 35: 554–558 (1963).
J.B. Ragland and V. John Kinross–Wright, "Spectrofluorometric Measurement of Phenothazines", 36 Analytical Chemistry, vol. 36: 1356–1359 (1964).
Signey Udenfriend et al., J. Pharmacol. Expt. Thera., vol. 120: 26–32 (1957).
David M. Takahashi, Journal of Pharmaceutical Sciences, vol. 69, No. 2: 184–187 (Feb. 1980).
Brian J. Clark et al., Anal. Chimica Acta., vol. 70: 35–44 (1985).
Minoru Nakano et al., Biochemical and Biophysical Research Communications, vol. 130, No.3 952–956 (1985).
M.A. Trush et al., Chem.–Biol. Interactions, vol. 28: 71–81 (1979).

J.K. Leland and M.J. Powell, J. Electrochem. Soc., vol. 137, No. 10: 3127–3131 (1990).
Xiao–Hong Hu and Allen J. Bard, Langmuir, vol. 10 2409–2414 (1994).
Luiz H. Catalani et al., Photochemistry and Photobiology, vol. 45, No. 2: 273–281 (1987).
Henry Gilman and Dhairyasheel R. Swayampati, J. Am. Chem. Soc., vol. 79: 208–212 (1957).
Csaba P. Keszthelyi et al., Journal of the American Chemical Society, vol. 94: 1522–1527 (1972).
James B. Noffsinger and Neil D. Danielson, Anal. Chem., vol. 59, 865–868 (1987).
Israel Rubinstein and Allen J. Bard, J.A. Chem. Soc., vol. 103; 512–516 (1981).
Deniz Eze et al., Anal. Chem., vol. 56: 2413–2417 (1984).
Henry S. White and Allen J. Bard, Journal of the American Chemical Society, vol. 104, No. 25: 6891–6895 (Dec. 1982).
A. Juris et al., Coordination Chemistry Review, vol. 84 85–277 (1988).
John A. Holeman and Neil D. Danielson, Analytica Chemica Acta, vol. 277 55–60 (1993).
Margaret A. Targove and Neil D. Danielson, Journal of Chromotographic Science, vol. 28, 505–509 (1990).
D.D.M. Wayner et al., "Oxidation and Reduction Potentials of Transient Free Radicals", J. Am. Chem. Soc., vol. 110 132–137 (1988).
R. Memming, "Mechanism of the Electochemical Reduction of Persulfates and Hydrogen Perioxide", J. Electrochem., Soc., vol. 116, No: 6: (Jun. 1969).
Larry R. Faulkner and Allen J. Bard, Journal of the American Chemical Society, vol. 90, No. 23: 6284–6290 (Nov. 1968).
Larry H. Faulkner and Allen J. Bard, "Techniques of Electrogenerated Chemiluminescence", Electoanalytical Chemical, vol. 10: 1 (1977).
Paul McCord and Allen J. Bard, J. Electranal. Chem., vol. 91: 318 (1991).
G.J. Siegel et al., 3rd edition, Basic Neurochemistry, Little, Brown and Co., Boston, 1981.
N.D. Danielson et al., Pharm. Biomed. Anal., vol. 7 1281 (1989).

(List continued on next page.)

*Primary Examiner*—W. Gary Jones
*Assistant Examiner*—Dianne Rees
*Attorney, Agent, or Firm*—Whitman Breed Abbott & Morgan, LLP

[57] ABSTRACT

Biomolecule analysis using anodic oxidation of aqueous sodium 9, 10-diphenylanthracene-2-sulfonate (DPAS) and 1- and 2-thianthrenecarboxylic acid (1-THCOOH and 2-THCOOH) in the presence of tri-n-propylamine (TPrA) as a coreactant in aqueous solution produces electrogenerated chemiluminescence (ECL). In addition, the cathodic reduction of DPAS in the presence of peroxydisulfate ($S_2O_8^{2-}$) as a coreactant also produces ECL in an acetonitrile (MeCN) -water solution (1:1 by volume). The oxidation of chlorpromazine (CPZ) produces an ECL emission in the absence of an added coreactant following an unprecedented "self-annihilation" mechanism.

21 Claims, 20 Drawing Sheets

OTHER PUBLICATIONS

A.J. Bard and L.R. Faulkner, "Electrochemical Methods: Fundamentals and Applications", Wiley, New York p.701 (1980) vol. # not applicable.

W.E. Geiger in Journal of Organometallic Chemistry Library. W.C. Trogler, Ed Elsevier, Amsterdam vol. 22: p. 144 (1990).

L.A. Tinker and A.J. Bard, J. Electroanal. Chem., vol. 133: 275 (1982).

Robinson and McCreery J. of Electoanalytical Chem 182: 61–72; 1985.

Sakura et al. Analytica Chimica Acta 262: 49–57; 1992.

Dodge et al. J. of Organic Chem 55: 4190–4198; 1990.

U.S. Patent Application Serial No. 08/385,864 filed Feb. 9, 1995.

U.S. Patent Application SN 08/196,315.

Catalani et al. Photochemistry and Photobiology 45: 273–281; 1987.

White and Bard J. of the American Chemical Society 104: 6891–6895; 1982.

Tinker and Bard (of interest) J. Electroanal. Chem 133: 275–285; 1982.

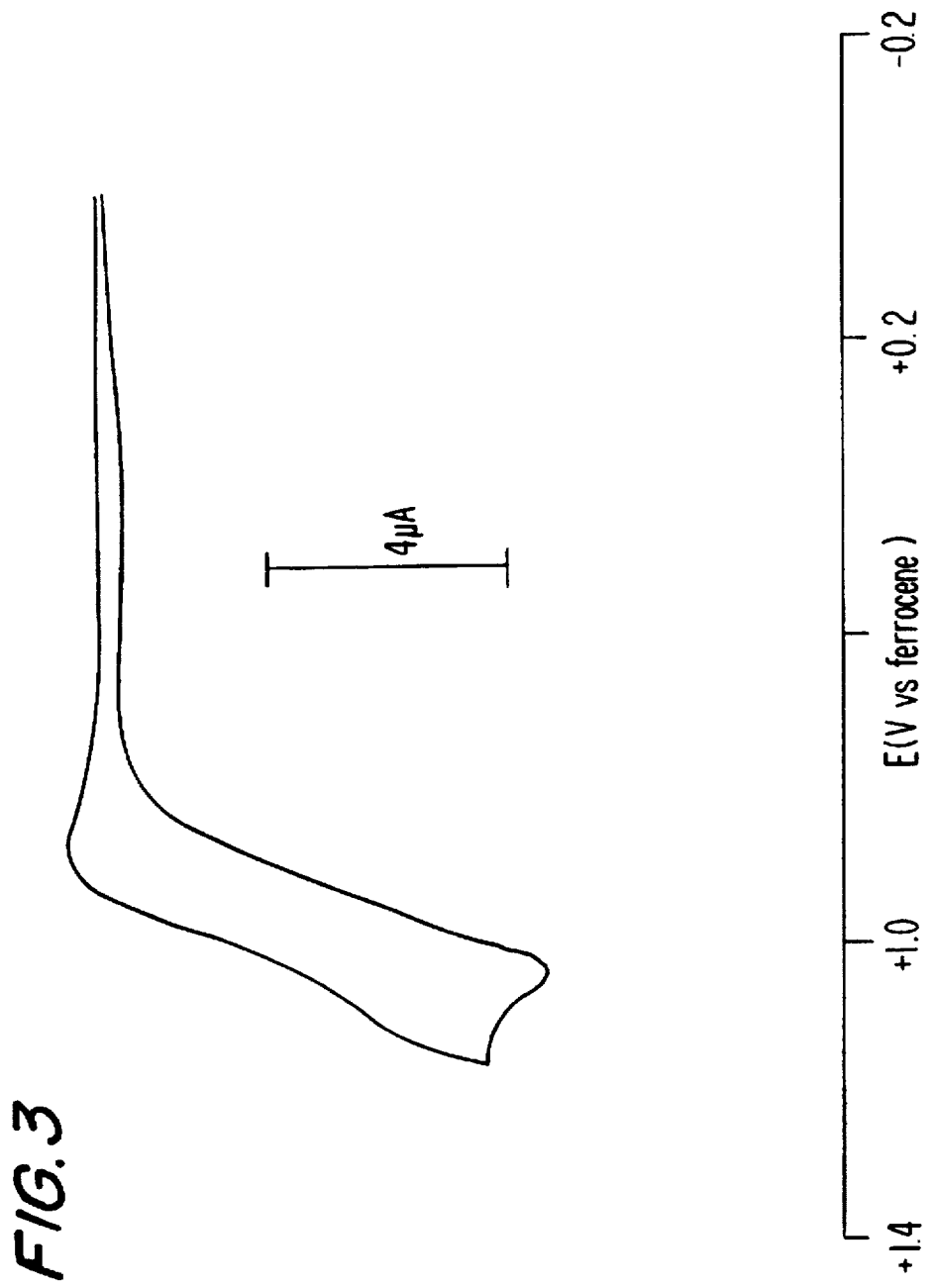

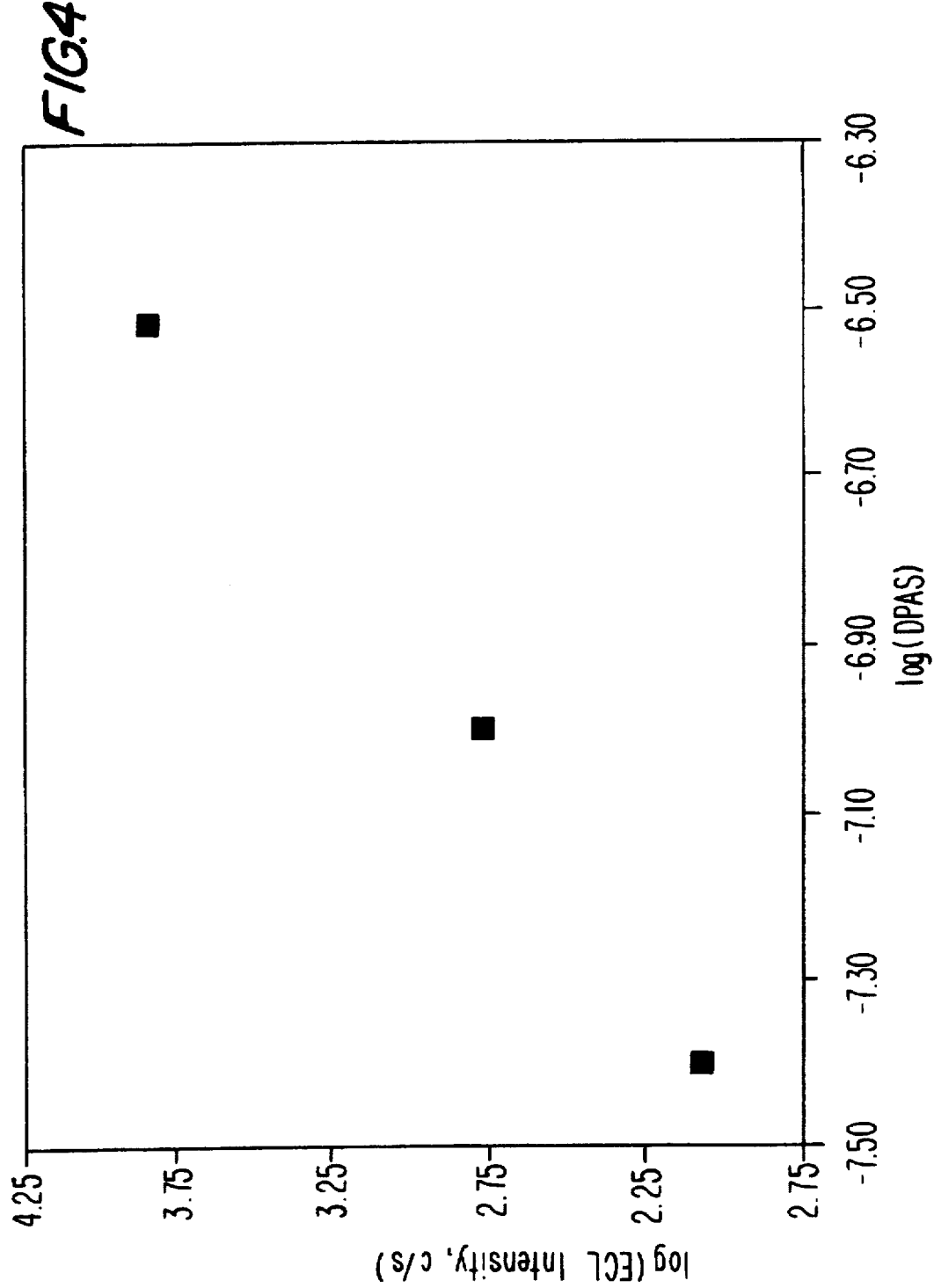

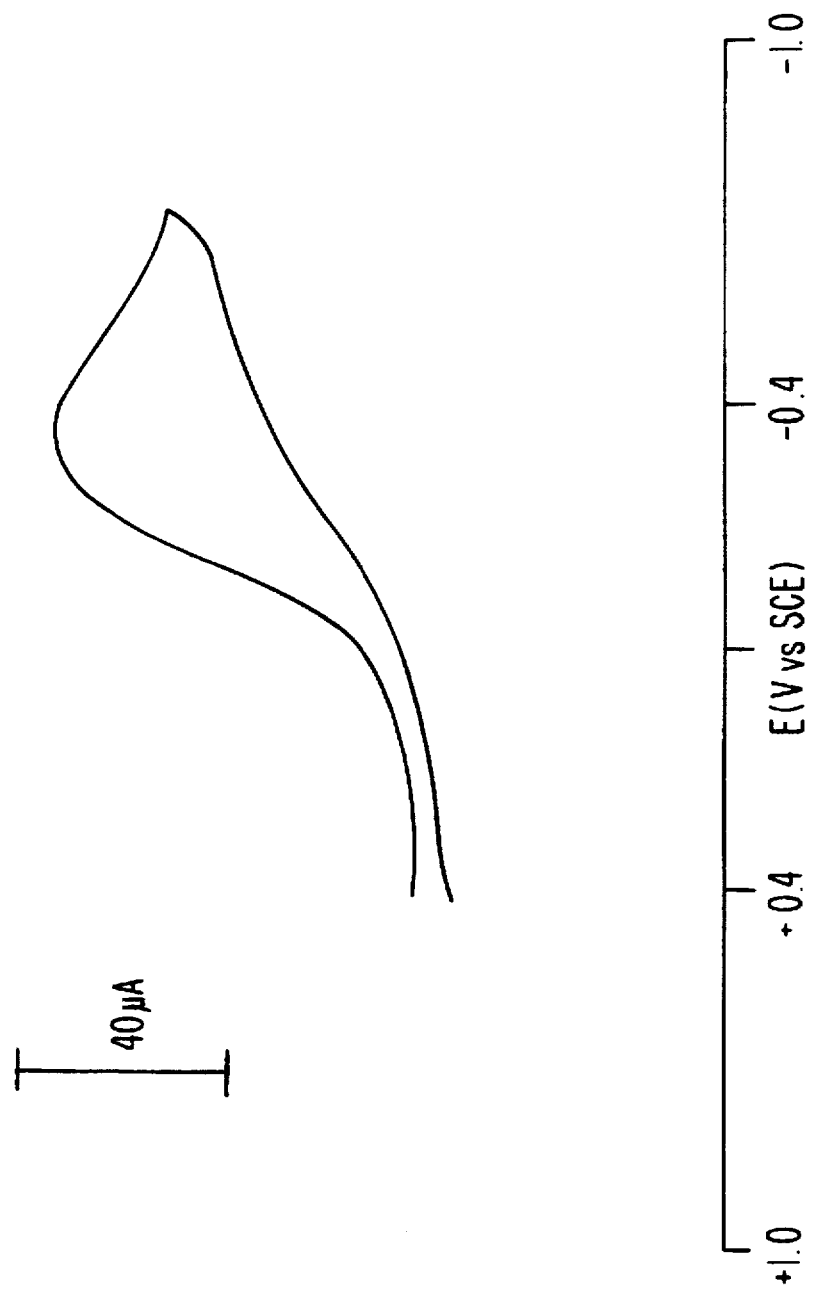

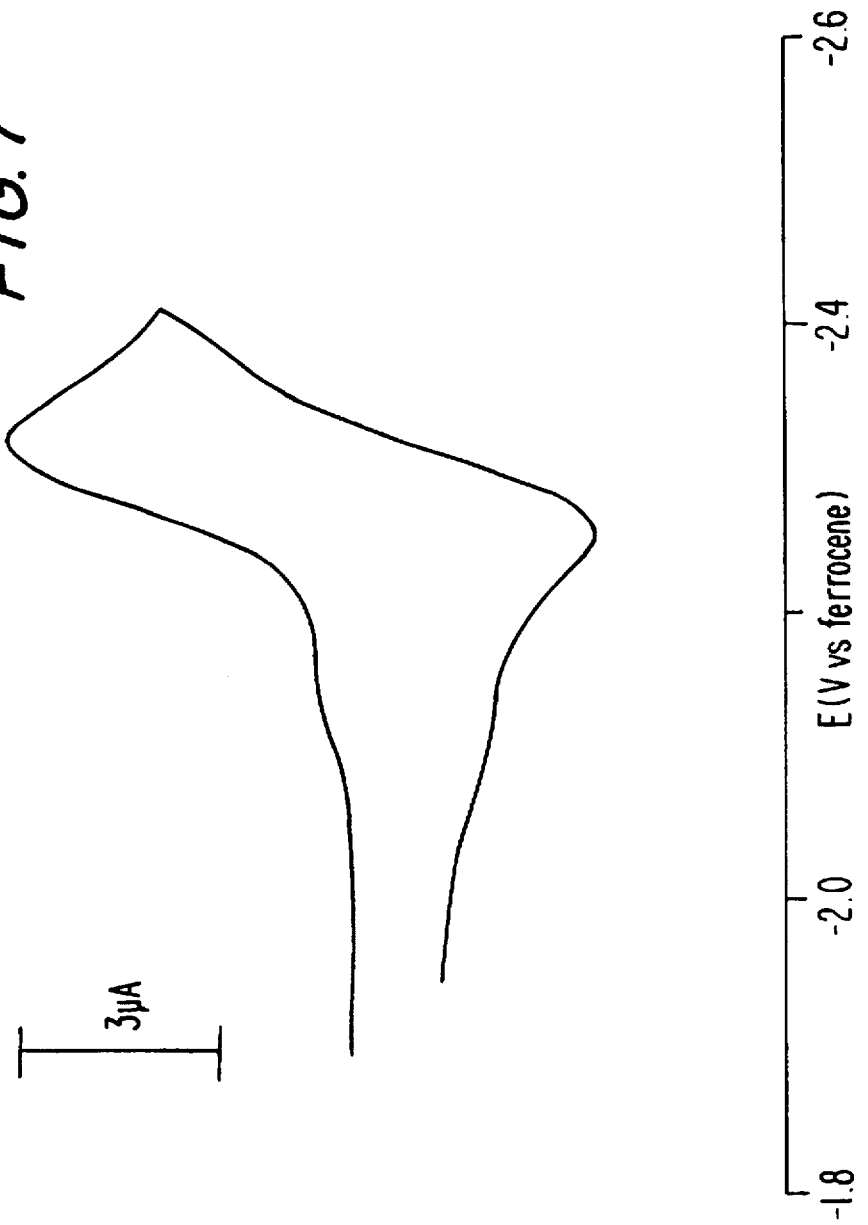

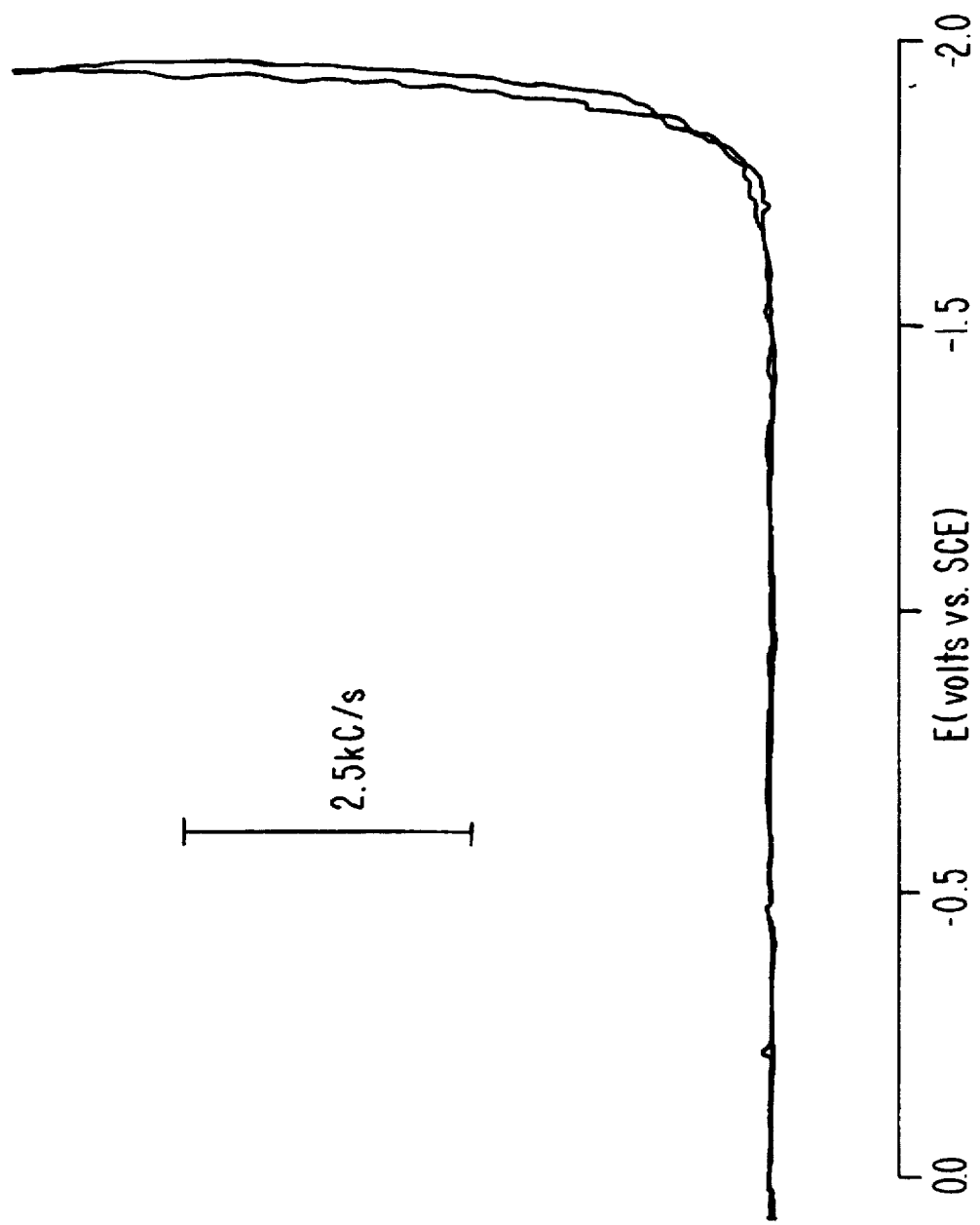

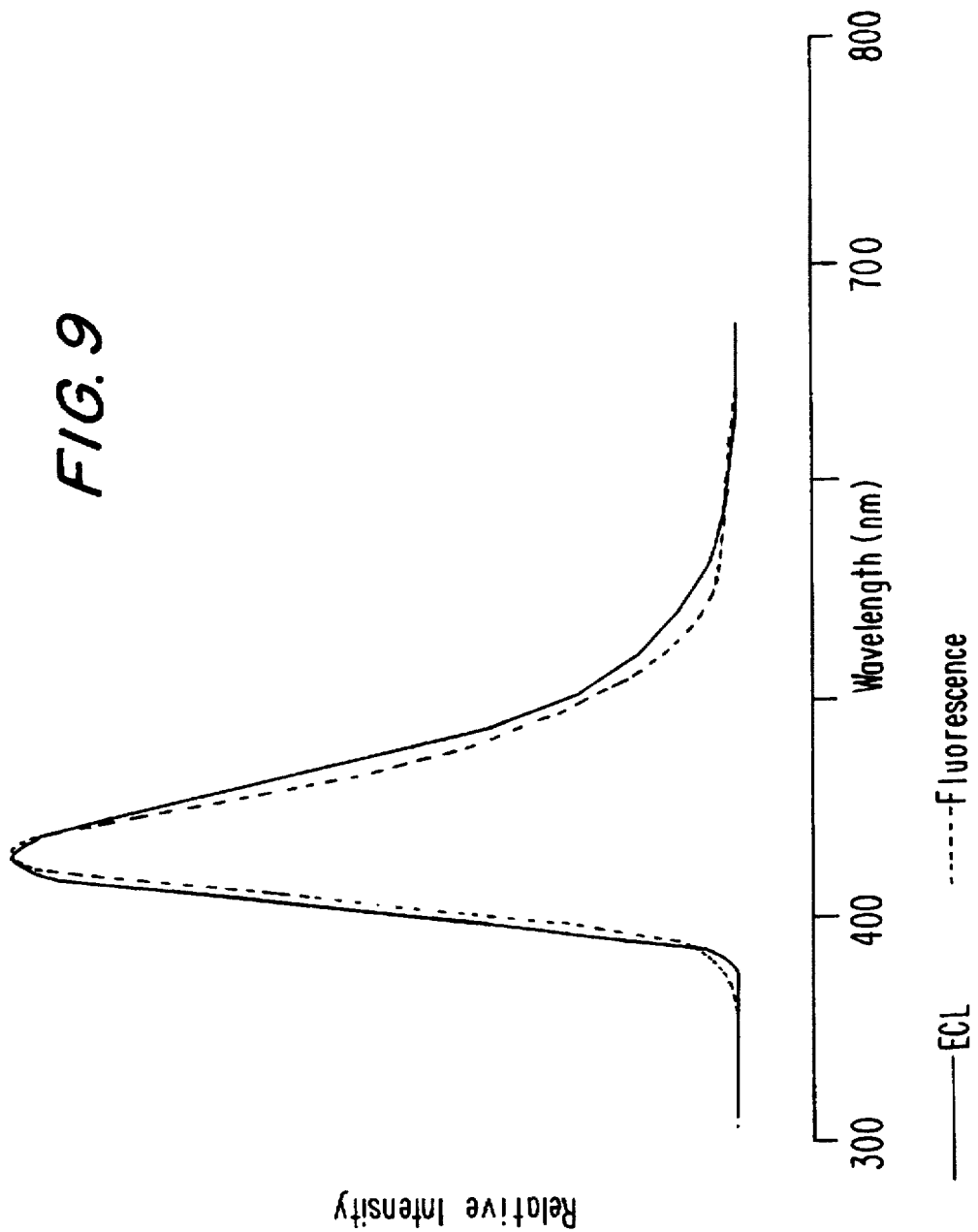

1-THCOOH
——ECL  ----Fluorescence

2-THCOOH
——ECL  ----Fluorescence

20 μA

+1.2  +1.0  E (V vs SCE)  +0.2  0.0

ELECTROGENERATED CHEMILUMINESCENCE LABELS FOR ANALYSIS AND/OR REFERENCING

RELATED APPLICATIONS

This application is a continuation-in-part of prior application Ser. No. 08/296,630 entitled, BIOSENSOR FOR AND METHOD OF ELECTROGENERATED CHEMILUMINESCENT DETECTION OF NUCLEIC ACID ON A SOLID SURFACE, in the names of Allan J. Bard and Xiaso-Hong Xu, filed on Aug. 26, 1994 now abandoned.

FIELD OF THE INVENTION

The present invention relates to electrogenerated chemiluminescent methods and compositions of modified hydrocarbons and aromatic heterocyclic compounds that occur in aqueous solutions with coreactants such as tri-n-propylamine (TPrA) and peroxydisulfate ($S_2O_8^{2-}$) and in particular, those that provide simultaneous analyses and internal referencing. More specifically, the present invention provides substituted polycyclic organic luminescing compounds that have ring carbons optionally replaced with at least one hetero atom selected from N and S, such as substituted diphenylanthracene, thianthrene and promazine, for electrogenerated chemiluminescent applications.

BACKGROUND OF THE INVENTION

Luminescing labels have been used to tag a variety of bioanalytes, such as enzymes, antibodies, antigens, peptides, nucleotides, saccharides or cells compliments of the analyte of interest, in immunoassays, DNA probe assays and fluorescent and separation assays. Of particular interest are labels which can be made to luminesce through electrochemical reaction schemes. Labels that luminesce as a result of electrochemical excitation are beneficial because of their sensitive and nonhazardous properties.

One analytical technique that exploits the benefits of these labels is electrogenerated chemiluminescence (ECL). ECL arises from an energetic electron transfer reaction between electrogenerated redox species represented by $A^-$ and $D^+$, typically radical ions, to form an excited state ($A^*$ or $D^*$) that emits in the visible region:

$$A + e^- \rightarrow A^- E_A \tag{1}$$

$$D - e^- \rightarrow D^+ E_D \tag{2}$$

$$A^- + D^+ \rightarrow A + D^* \text{ (or } A^* + D\text{)} \tag{3}$$

$$D^* \rightarrow D + h\upsilon \tag{4}$$

Faulkner and Bard in *Electroanalytical Chemistry*, Vol. 10, p. 1, 1977 provide several examples of nonaqueous systems of this type.

A. W. Knight and G. M. Greenway in the *Analyst*, 1994, 119, 879 discuss ECL precursors that can be generated in aqueous solution even with the limited potential range imposed by the oxidation and reduction of water. ECL can be achieved by the simultaneous oxidation of tris (2,2'-bipyridine)ruthenium(II) ($Ru(bpy)_3^{2+}$) and a coreactant ($XY^Z$) capable of generating a suitable reductant upon oxidation via an oxidative-reduction mechanism such as:

$$Ru(bpy)_3^{2+} - e^- \rightarrow Ru(bpy)_3^{3+} \tag{5}$$

$$XY^Z - e^- \rightarrow XY^{Z+1} \tag{6}$$

$$Ru(bpy)_3^{3+} + XY^Z \rightarrow Ru(bpy)_3^{2+} + XY^{Z+1} \tag{6a}$$

$$XY^{Z+1} \rightarrow X^x + Y^y \; (x+y=z+1) \tag{7}$$

$$Ru(bpy)_3^{3+} + X^x \rightarrow Ru(bpy)_3^{2+*} + X^{x+1} \tag{8}$$

$$Ru(bpy)_3^{2+*} \rightarrow Ru(bpy)_3^{2+} + h\upsilon \tag{9}$$

$Ru(bpy)_3^{2+}$ is a typical precursor (D) for these schemes and has been used in chemiluminescence (CL) reactions with amines as well as ECL investigations utilizing a number of different coreactants including oxalate (where $XY^Z$ is $C_2O_4^{2-}$ and $X^x$ is $CO_2^{-*}$) and aliphatic amines such as tri-n-propylamine (TPrA; where $XY^Z$ is $Pr_3N$ and $X^x$ is the radical that results from deprotonation of $Pr_3N^+$). In these ECL schemes, the coreactant can be oxidized either at the electrode via equation (6) or in solution by the emitter via equation (6a). As an alternative to the reaction scheme of equation (8), the excited state can also be generated by the sequence of equations (10) and (11), below, as previously discussed for oxalate and TPrA.

$$Ru(bpy)_3^{2+} + X^x \rightarrow Ru(bpy)_3^+ + X^{x+1} \tag{10}$$

$$Ru(bpy)_3^+ + Ru(bpy)_3^{3+} \rightarrow Ru(bpy)_3^{2+*} + Ru(bpy)_3^{2+} \tag{11}$$

For the oxalate coreactant, the reaction scheme of equation (7) involves cleavage of the carbon-carbon bond while for the TPrA coreactant it is believed that this step involves the loss of a proton from the α-carbon. These ECL reactions have been used for the determination of both $Ru(bpy)_3^{2+}$ and oxalate.

To complement these oxidative-reduction examples, peroxydisulfate and $Ru(bpy)_3^{2+}$ undergo an analogous inversion of this scheme (a reductive-oxidation mechanism, equations (12)–(14) followed by (9)) when the initial reactants are reduced, rather than oxidized, in acetonitrile (MeCN)-water solutions (1:1 volume ratio). In this case, the reduction of $S_2O_8^{2-}$ results in the formation of the strong oxidizing agent $SO_4^{-*}$:

$$Ru(bpy)_3^{2+} + e^- \rightarrow Ru(bpy)_3^+ \tag{12}$$

$$S_2O_8^{2-} + e^- \rightarrow SO_4^{-*} + SO_4^{2-} \tag{13}$$

$$Ru(bpy)_3^+ + S_2O_8^{2-} \rightarrow Ru(bpy)_3^{2+} + SO_4^{-*} + SO_4^{2-} \tag{13a}$$

$$Ru(bpy)_3^+ + SO_4^{-*} \rightarrow Ru(bpy)_3^{2+*} + SO_4^{2-} \tag{14}$$

By analogy to equations (10) and (11) for oxalate and TPrA, an alternative to equation (14) for generating the excited state with peroxydisulfate is:

$$Ru(bpy)_3^{2+} + SO_4^{-*} \rightarrow Ru(bpy)_3^{3+} + SO_4^{2-} \tag{15}$$

followed by equation (11) above.

The sensitivity and selectivity of these coreactant analyses has led to the recent commercial application of the $Ru(bpy)_3^{2+}$/TPrA system. For example, electrochemiluminescent ruthenium- and osmium-containing labels have been used in methods for detecting and quantifying analytes of interest in liquid media, U.S. Pat. Nos. 5,310,687; 5,238,808; and 5,221,605, incorporated herein by reference. In addition, the application of electrogenerated chemi-luminescence (ECL) measurements to the detection of solution phase DNA intercalated with ruthenium-containing labels has been described (Carter, M. T. et al. (1990) *Bioconjugate Chem* 2:257–263). Although such applications provide an accept-

3 able analysis technique, it is often necessary to provide a system that allows simultaneous analyses and internal referencing. The present invention provides additional electrochemiluminescent systems that may be used in place of or along side of existing systems.

SUMMARY OF THE INVENTION

The present invention relates to new labels where: 1) the emitter must be soluble in aqueous solution; 2) the emission wavelength must be distinct from that of $Ru(bpy)_3^{2+*}$; 3) the oxidative or reductive electrochemistry must proceed within the relatively narrow potential range imposed by the oxidation and reduction of water; and 4) the oxidized or reduced intermediate must react with the electrogenerated coreactant intermediate allowing formation of the excited state.

An object of the present invention is to provide substituted polycyclic organic luminescing compounds, e.g., aromatic polycyclics, that may have ring carbon substitutions selected from at least one hetero N or S atom having these four (4) properties. Substituted diphenylanthracene, thianthrene and promazine exemplify such reagent systems for electrogenerated chemiluminescent applications.

Another object of the present invention is to provide substituted polycyclic organic luminescing compounds, e.g., aromatic polycyclics, that may have ring carbon substitutions, that offer a complementary label to $Ru(bpy)_3^{2+}$ in bioanalytical applications.

It is an object of the present invention to provide label-coreactant compositions that allow for simultaneous analyses.

It is a still further object of the present invention to provide a method of detecting a plurality of analytes by (1) providing at least a first biomolecule with a luminescent label that has an emission wavelength distinct from that of $Ru(bpy)_3^{2+*}$; (2) providing a second biomolecule analyte with a ruthenium or osmium containing label; (3) adding at least one coreactant; and (4) exposing the labelled biomolecule analytes and coreactants to electrochemical reaction or excitation and measuring the resulting luminescence to detect the various biomolecule analytes present.

A further object of the present invention is to provide a composition involving the anodic oxidation of aqueous sodium 9,10-diphenylanthracene-2-sulfonate (DPAS) in the presence of tri-n-propylamine and the cathodic reduction of DPAS in the presence of peroxydisulfate ($S_2O_8^{2-}$) as a coreactant in an acetonitrile (MeCN)-water solution (1:1 by volume) for ECL analysis of biomolecules (i.e., immunoassays, DNA probes). When sodium 9,10-diphenylanthracene-2 sulfonate is oxidized in the presence of TPrA or reduced with $S_2O_8^{2-}$, a blue ECL emission results which is characteristic of DPAS fluorescence. The spectral separation between this emission and that for $Ru(bpy)_3^{2+}$ makes DPAS a complementary label to $Ru(bpy)_3^{2+}$ in bioanalytical applications.

A still further object is providing 1- and 2-thianthrenecarboxylic acid (1-THCOOH and 2-THCOOH) in the presence of tri-n-propylamine (TPrA) as a coreactant in aqueous solution for electrogenerated chemiluminescence (ECL) for ECL analysis of biomolecules (i.e., immunoassays, DNA probes.

A still further object is to provide an ECL scheme of oxidizing chlorpromazine without added coreactant (TPrA) to produce an ECL emission via an unprecedented self-annihilation reaction.

These and other objects, advantages and salient features of the present invention will become more apparent from the following detailed description, non-limiting examples and annexed drawings.

BRIEF DESCRIPTION OF DRAWINGS

FIG. 3 shows the cyclic voltammogram of 0.92 mM DPAS in MeCN at a 1.5 mm dia. Pt electrode. Supporting electrolyte, 0.1M $TBABF_4$; scan rate, 200 mV/s.

FIG. 4 is a log-log plot of DPAS ECL intensity vs concentration for solutions containing 0.15M TPrA in pH 7.5 sodium phosphate buffer.

FIG. 6 shows the cyclic voltammogram of 11 mM $(NH_4)_2S_2O_8$ in an MeCN-water solution (1:1 volume ratio) at a 1.5 mm dia. Pt electrode. Supporting electrolyte, 0.2M TEAP; scan rate, 100 mV/s.

FIG. 7 shows the cyclic voltammogram of 0.93 mM DPAS in MeCN at a 1.5 mm dia. Pt electrode. Supporting electrolyte, 0.1M $TBABF_4$; scan rate, 200 mV/s.

FIG. 8 shows the ECL emission for the reduction of 1.1 mM DPAS and 25 mM $(NH_4)_2S_2O_8$ in MeCN-water solution (1:1 volume ratio) at a 2.0 mm dia. Pt electrode. Supporting electrolyte, 0.2M TEAP; scan rate, 100 mV/s.

FIG. 9 shows the fluorescence and ECL spectra for the same solution as FIG. 8. The ECL emission was generated by pulsing a 2.0 mm dia. Pt electrode to −2.2 V (vs SCE) and integrating the emission for 5 s. Both peak intensities are at 430 nm.

FIG. 13 shows a cyclic voltammogram of 2.0 mM 2-THCOOH in the presence of 0.05M TPrA. Other conditions are the same as in FIG. 10a.

FIGS. 21a–21c show excitation voltage and intensity ramps.

DETAILED DESCRIPTION OF THE INVENTION

Figure 1:
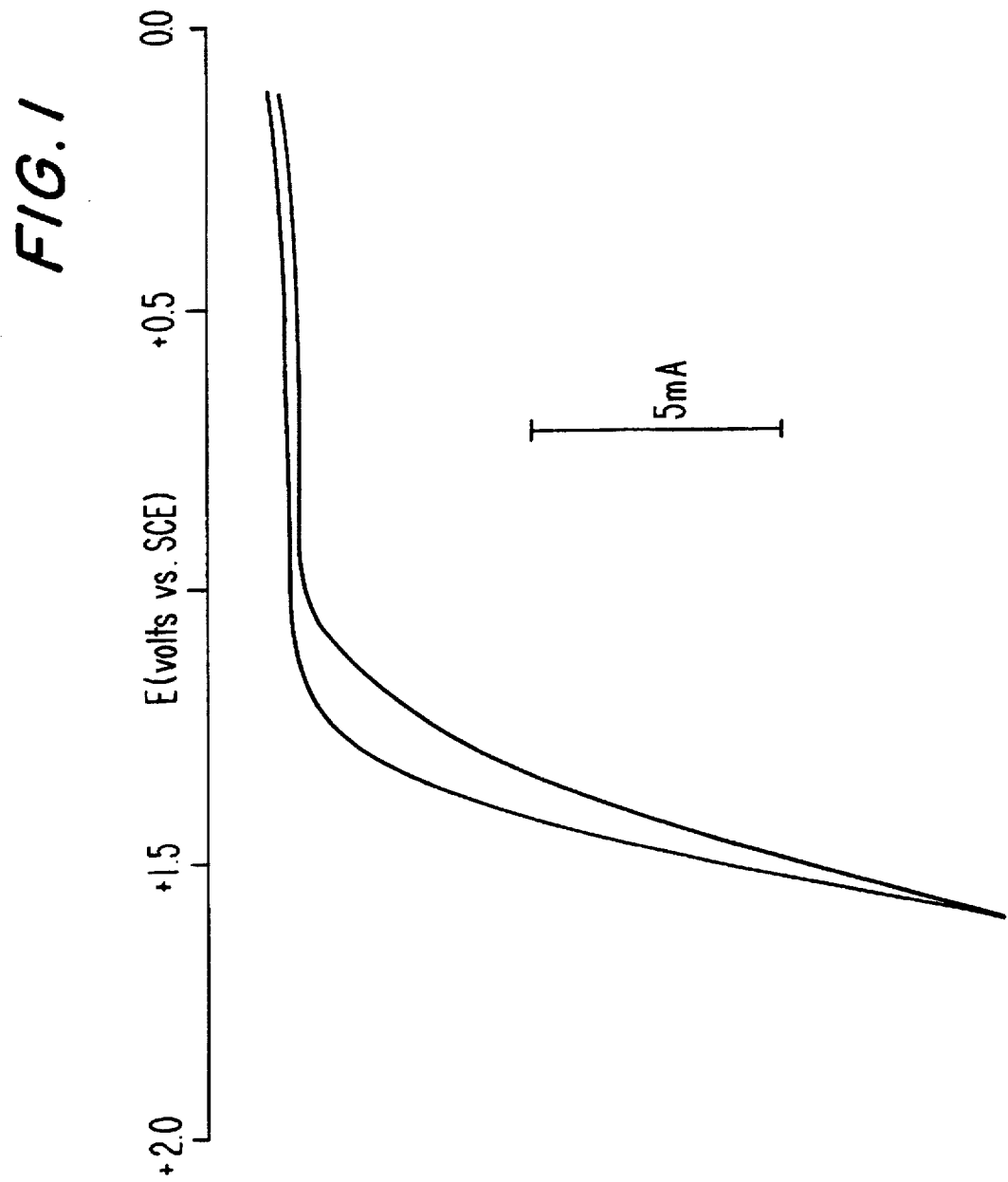
FIG. 1 shows the cyclic voltammogram of the background oxidation of water in the presence of $1\times10^{-5}$M DPAS in pH 7.5 sodium phosphate buffer at a 6×9 mm Pt gauze (52 mesh) electrode. Scan rate, 100 mV/s.

In the present invention, the electrogenerated chemiluminescence composition requires that: 1) the emitter must be soluble in aqueous solution; 2) the emission wavelength must be distinct from that of Ru(bpy)$_3^{2+}$*, 3) the oxidative or reductive electrochemistry must proceed within the relatively narrow potential range imposed by the oxidation and reduction of water; and 4) the oxidized or reduced intermediate must react with the electrogenerated coreactant intermediate allowing formation of the excited state. Satisfying these criteria allows the new compositions to be used independently of, or along with existing Ru(bpy)$_3^{2+}$ systems. Labels that can be used with the ruthenium labels are substituted polycyclic organic luminescing compounds, e.g., aromatic polycyclics, that may have ring carbon substitutions of at least one hetero atom, N and or S, their isomers and salts thereof. Preferred polycyclics include, but are not limited to, substituted diphenylanthracene, thianthrene and promazine and are used for electrogenerated chemiluminescent applications.

A preferred label according to the present invention is DPAS that is a strongly fluorescent excited-state

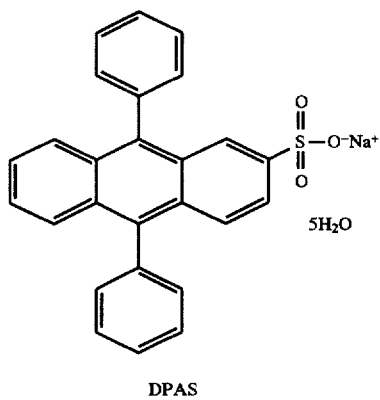

DPAS energy acceptor from singlet ketones in aqueous media possessing high fluorescence efficiency and short wavelength emission ($\phi_f$=0.87, peak emission at 428 mm) compared to Ru(bpy)$_3^{2+}$($\phi_f$, about 0.05, peak emission at 620 nm). DPAS therefore satisfies the above criteria and produces blue ECL emission resulting from an oxidative-reduction scheme involving DPAS as the emitter and TPrA as the coreactant in aqueous media. Additionally, the ECL of DPAS in a reductive-oxidation scheme using peroxydisulfate (S$_2$O$_8^{2-}$) as a coreactant in an MeCN-water solution (1:1 volume ratio) also satisfies the above criteria.

Another preferred embodiment involves two carboxylic acid derivatives of thianthrene (TH), namely 1- and 2-thianthrenecarboxylic acid (1-THCOOH and 2-THCOOH) and their isomers.

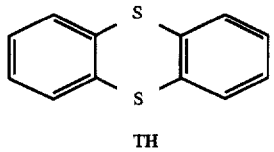

TH

Thianthrene is known to produce ECL (peak intensity at 434 nm) in a non-aqueous ion annihilation scheme following equations (1)–(4) above. Derivatization of TH to its carboxylic acid

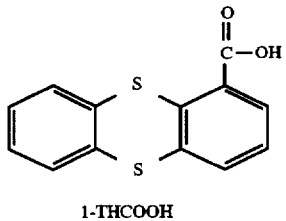

1-THCOOH

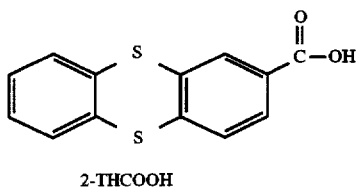

2-THCOOH derivatives afforded the necessary solubility in aqueous solution and these derivatives produced ECL emissions in an oxidative-reduction scheme with TPrA as a coreactant. However, unlike thianthrene that has a blue ECL emission, the ECL spectra of these compounds are significantly red-shifted, however, from the fluorescence spectra.

Another preferred embodiment according to the present invention involves aqueous ECL with chlorpromazine (CPZ), which is structurally related to TH. Although the fluorescence, chemiluminescence and electrochemistry of CPZ have been studied, its use for ECL applications have not. McCreery studied the oxidation of CPZ and various reactions of the cation radical described in (Cheng, H. Y.; Sackett, P. H.; McCreery, R. L. *J. Am. Chem. Soc.* 1978, 100,962.), and more recently, extended the work to consider the reaction of the chlorpromazine cation radical with dopamine described in (Deputy, A.; Wu, H. P.; McCreery, R. L. *J. Phys. Chem.* 1990, 94, 3620) and (Deputy, A. L.; McCreery, R. L. *J. Electroanal. Chem.* 1989, 285, 1.), methoxypromazine (Deputy, A. L.; McCreery, R. L. *J. Electroanal. Chem.* 1989, 285, 1.) and hydroquinone (Deputy, A. L.; McCreery, R. L. *J. Electroanal. Che.* 1989, 285, 1.). In addition, the fluorescence described in (Mellinger, T. J.; Keeler, C. E. *Anal Chem.* 1964, 36, 1840.; Mellinger, T. J.; Keeler, C. E. *Anal. Chem.* 1963, 35,554.; Ragland, J. B.; Kinross-Wright, V. J. *Anal. Chem.* 1964, 36, 1356.; and Udenfriend, S.; Duggan, D. E.; Vasta, B. M.; Brodie, B. B. *J. Pharmacol. Expt. Thera.* 1957, 120, 26.)

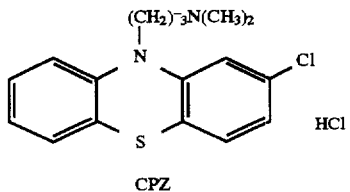

CPZ (including analytical applications (Takahashi, D. M. *J. Pharm. Sci.* 1980, 69, 184.) and (Clark, B. J.; Fell, A. F.; Milne, K. T.; Pattie, D. M. G.; Williams, M. H. *Anal. Chim. Acta.* 1985, 170, 35.)) and chemiluminescence described in (Nakano, M.; Sugioka, K.; Nakano, H.; Takyu, C.; Inaba, H. *Biochem. Biophys. Res. Commun.* 1985, 130, 952) and (Trush, M. A.; Reasor, M. J.; Wilson, M. E.; Van Dyke, K. *Chem.-Biol. Interact.* 1979, 28, 71.) of chlorpromazine have been investigated. In addition to emitting light in an oxidative-reduction scheme with TPrA, CPZ also emits when oxidized in the absence of an added coreactant. Presumably, the tertiary amine on the CPZ side chain acts as an internal coreactant and is believed to provide the first example of a "self-annihilation" ECL reaction.

REAGENTS

MeCN was transferred unopened into a Vacuum Atmospheres glovebox under helium atmosphere and was otherwise used as received. For experiments run in MeCN, a sealed cell was loaded in the glovebox prior to each experiment. Tetrabutylammonium tetrafluoroborate (TBABF$_4$, electrometric grade), was purified by recrystallization from either ethyl acetate:pentane (2 times; 1:1 volume ratio) or ethyl acetate:diethyl ether (3 times; 9:1 volume ratio) followed by drying under vacuum at 100° C. Tetraethylammonium perchlorate, (TEAP, electrometric grade wet with 8% water, tri-n-propylamine (TPrA, 98%.), thianthrene (97%), chlorpromazine hydrochloride (98%) sodium phosphate, monobasic monohydrate (NaH$_2$PO$_4$.H$_2$O, 99%), sodium phosphate, dibasic heptahydrate (Na$_2$HPO$_4$.7H$_2$O, 99%, and ammonium peroxydisulfate (NH$_4$)$_2$S$_2$O$_8$.99%, were used as received.

BUFFER 0.15M sodium phosphate buffer solutions prepared with Milli-Q water (Millipore Corp., Bedfore, Wash.) were 0.10M in Na$_2$HPO$_4$.7H$_2$O and 0.05M in NaH$_2$PO$_4$.H$_2$O. Buffer solutions containing TPrA were prepared similarly except that 0.15M NaH$_2$PO$_4$.H$_2$O was used to offset the basicity of TPrA. The pH of these buffer solutions was adjusted with either concentrated phosphoric acid (H$_3$PO$_4$) or 4M NaOH.

INSTRUMENTATION

Cyclic voltammetry without photon detection was obtained by using either a BAS 100A Electrochemical Analyzer (Bioanalytical Systems, West Lafayette, Ind.) or a Princeton Applied Research (PAR) model 173/175 potentiostat/universal programmer (Princeton, N.J.) and Omnigraphic 20000 X-Y recorder (Bausch and Lomb-Houston Instrument Division, Austin, Tex.). Cyclic voltammograms with simultaneous photon detection were recorded using the PAR 173/175 in conjunction with a Hamamatsu C1230 photon counter (Bridgewater, N.J.) equipped with a Hamamatsu R928-P photomultiplier tube. The photomultiplier tube was housed in a water jacketed Products For Research, Inc. model TE308TSRF refrigerated chamber maintained at −10° C. Primary cooling of the water jacket to 10° C. was accomplished using an MGW Lauda model RMS6 refrigeration unit (sold by Brinkmann Instruments Co., Westbury, N.Y.). For plots of ECL intensity vs. potential, the output from the photon counter was fed into the Y-axis of the X-Y recorder during potential scans.

ECL Intensity vs. concentration and ECL intensity vs pH data were acquired using Perkin-Elmer's prototype ECL analyzer (Perkin-Elmer Corp., Norwalk, Conn.; model QPCR System 5000; similar to the instrument described in Leland, J. K.; Powell, M. J. *J. Electrochem. Soc.* 1990, 137, 3127. This instrument is interfaced with a Digital DEC station 316SX personal computer.

Fluorescence and ECL spectra were recorded using a charge-coupled device (CCD) camera and spectrometer (1 mm entrance slit) interfaced to a Dell System 200 personal computer (Austin, Tex.) as previously described. The same procedures (spectral calibration etc.) were followed except that different pulse sequences were used and the CCD detector was maintained at −110° C. for the TPrA/THCOOH and TPrA/DPAS experiments and −100° C. for the S$_2$O$_8^{2-}$/DPAS experiments. Excitation for the fluorescence spectra was achieved by holding a longwave (366 nm) UV lamp (UVP, Inc., San Gabriel, Calif.; model UVGL-25; sold by Fisher Scientific, Pittsburgh, Pa.) next to the cell and at right angles to the entrance slit of the spectrometer.

CELLS AND ELECTRODES

Except where noted, all electrochemical and ECL experiments utilized a conventional 3-electrode cell configuration. Pt disk working electrodes were polished on a felt pad (Buehler, Ltd., Lake Bluff, Ill.) before each experiment run with 0.05 μm alumina (Buehler, Ltd.) suspended in water.

The cell for the Perkin-Elmer instrument was modified so that: 1) the thin-layer flow cell utilizes one working electrode (Au) and two square (5×5 mm) counter electrodes (both Au); 2) the two counter electrodes are placed above and flanking the working electrode in the flow cell with the working electrode in direct view of the photomultiplier tube; and 3) the Ag/AgCl reference electrode is situated in a compartment beside the flow cell instead of being incorporated into the flow path downstream for the cell. Electrodes in this instrument were cleaned electrochemically before each run using commercially available cleaning solution (IGEN Inc., Rockville, Md.) in combination with a programmed potential pulse sequence.

For cyclic voltammetry runs without photon detection, the CPZ embodiment utilized a highly-oriented pyrolytic graphite (HOPG; Union Carbide, Cleveland, Ohio) working electrode (6 mm dia. disk with freshly exposed material for each experiment), Pt wire counter electrode and Ag quasireference electrode (AgQRE) in a recently describe configuration. See Xu, X.; Bard, A. J. Langmuir, 1994, 10, 2409. Similar runs for all other compounds utilized a 1.5 mm diameter Pt disk working electrode sealed in glass in combination with a Pt wire counter electrode and AgQRE.

The DPAS/TPrA ECL spectrum and emission vs. potential scans utilized a 6×9 mm Pt gauze flag (52 mesh gauze; Aldrich) working electrode, an AgQRE and a round (9 mm diameter, 0.5 mm thick) Au foil counter electrode. The 2-THCOOH ECL spectrum also utilized this arrangement. The gauze working electrode was cleaned prior to each experiment by immersion in concentrated nitric acid followed by rinsing in distilled water and heating in a bunsen burner flame.

The DPAS/$S_2O_8^{2-}$ ECL spectrum and emission vs. potential scan utilized a 2.0 mm diameter Pt disk working electrode sealed in glass in combination with a Pt wire counter electrode and AgQRE.

The CPZ ECL emission vs. potential scan utilized the same electrodes and configuration described above for CPZ without photon detection. ECL emission vs potential for 2-THCOOH utilized the same arrangement except that the working electrode was a 6 mm dia Pt disk.

Nonaqueous potential referencing to ferrocene was accomplished by adding the standard directly to the solutions. Potential referencing of aqueous solutions to the saturated calomel electrode (SCE) was accomplished by acquiring data vs an AgQRE for which the potential vs. SCE was known. For qualitative comparison purposes, the ferrocene $E°$ vs. SCE varies (due primarily to differences in liquid junction potentials) from +0.307 to +0.56 V depending upon the solvent/supporting electrolyte system.

EXAMPLE 1

DPAS was synthesized following variations on the procedure of Catalani and coworkers described in Catalani, L. H.; Wilson, T.: Bechara, E. J. H. Photochem. Photobiol. 1987, 45,273. Thus, 1 g of 9,10-diphenylanthracene (DPA, 98%;) was suspended in 7 mL of nitrobenzene (99%) and the resulting yellow suspension was cooled to 10° C. in an ice bath under a steady flow of nitrogen. With vigorous stirring, 0.25 mL of fuming sulfuric acid (27–33% free $SO_3$) was added dropwise to produce a dark green suspension which was initially stirred at 50° C. for 4 hours followed by overnight stirring at room temperature. The dark green solution was then neutralized with 10M NaOH in an ice bath to produce an oily, pale yellow residue. When pH paper wetted with this suspension first changed to an orange-red color instead of the initial deep red color, 50 mL of water was added to the mixture before the final addition of NaOH to bring the pH to 7.0. Additional water was then added to bring the total volume to about 250 mL and the nitrobenzene was removed by steam distillation (affected by boiling the suspension). Most of the nitrobenzene was removed with the first 75 mL of distillate and the distillation was continued until the suspension volume was about 50 mL. The yellow suspension was then transferred to a beaker and boiled on a hot plate with stirring to reduce the total volume to about 10 mL. The yellow slurry was filtered over a buchner funnel (with filter paper) and the resulting solid allowed to air dry to produce 0.94 g of crude yellow product. The crude product was purified by ion-exchange column chromatography using Dowex 1×2-100 ion-exchange resin (50–100 dry mesh; 3×1 cm) and elution with a gradient of 0–0.5M HCl (mixed from 36.5% HCl; in anhydrous methanol (spectrophotometric grade). Thus approx. 0.35 g of crude yellow product was dissolved in 10 mL of methanol with stirring and sonication. Unreacted DPA present in the crude product is only slightly soluble in methanol and was thus separated by centrifugation. The supernatant was applied to the column and the product eluted with about 5 mL methanol followed by about 5 mL of 0.25M HCl in methanol followed by 0.5M HCl in methanol. Nine 20-mL fractions were collected and 60 mL of water was added to each fraction. Fractions 1–5 showed cloudiness and/or precipitate formation and were cooled in a refrigerator overnight. The solid product was then separated by centrifugation and filtration over a fine, sintered-glass frit. When the flow of liquid through the frit stopped due to clogging, the greenish, jelly-like slurry was transferred to a glass petri dish, covered with a piece of filter paper, and allowed to air-dry for several days under ambient conditions. When dry, 110 mg of light yellow-green DPAS.$5H_2O$ was scraped from the petri dish with a razor blade and characterized by $^1H$ NMR and mass spectrometry.

Figure 2A:
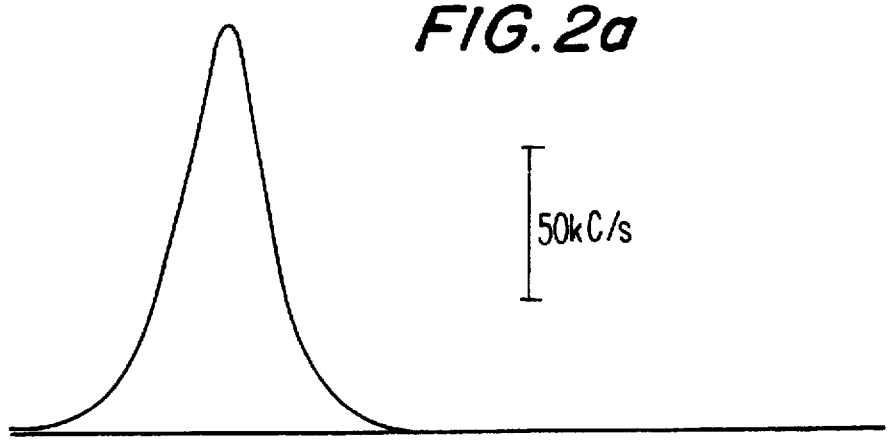
FIGS. 2a–2c show the emission (a) during cyclic voltammetry (b) of $1\times10^{-5}$M DPAS and 0.15M TPrA in pH 7.5 sodium phosphate buffer at 6×9 mm Pt gauze (52 mesh) electrode. Scan rate, 100 mV/s. (c) Cyclic voltammogram of 0.05M TPrA in pH 7.5 sodium phosphate buffer at a 1.5 mm dia. Pt electrode. Scan rate, 200 mV/s.
Figure 2B:
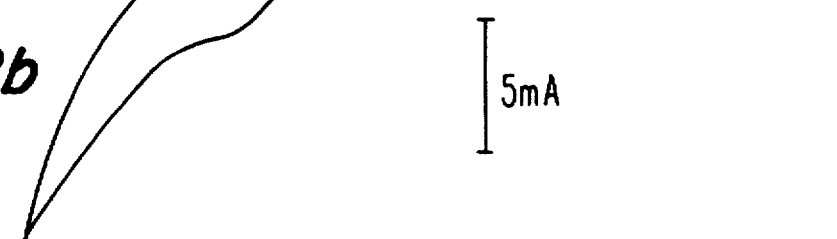
Figure 2C:

Aqueous solutions of DPAS.$5H_2O$ were prepared by dissolving the required amount of solid in a few drops of methanol prior to transfer to the aqueous solution. The maximum solubility of aqueous DPAS in 0.15M sodium phosphate buffer (pH 7.5) is approximately $1\times10^{-5}$M. At this low concentration, no anodic current can be observed for DPAS above the background oxidation of water as shown in FIG. 1. However, if $1\times10^{-5}$M DPAS is oxidized in the presence of 0.15M TPrA, an emission that coincides with an oxidation wave occurs that is superimposed on the TPrA oxidation and background oxidation of water as shown in FIGS. 2a–2b. For comparison, the oxidation of 0.05M TPrA in the absence of DPAS is shown in FIG. 2c. The fact that an oxidation current is observed for $1\times10^{-5}$M DPAS only in the presence of TPrA implicates a catalytic current enhancement due to the regeneration of DPAS via reduction of DPAS$^+$ by TPrA or an intermediate. For this catalysis, the cyclic sequence of reactions is analogous to equation schemes (5), (6a), (7), (8) or (10) and (11), and (9) above where Ru(bpy)$_3^{3+/2+/+}$ is replaced by DPAS$^{+/0/-}$ respectively, XY$^z$ is TPrA, X$^x$ is Pr$_2$NCH.Et and Y$^y$ is H$^+$. Despite the low DPAS concentration, $1\times10^{-5}$M, this emission is visibly blue when viewed in a dark room and no emission is observed in the absence of either TPrA or DPAS.

With respect to the ECL intensity as a function of pH, slightly more intense emissions were sometimes recorded at lower pH's but no conditions were found where these differences were outside experimental scatter. For the DPAS/TPrA system, electrode passivation occurs after one scan and prevents observation of subsequent emissions without electrode cleaning. This behavior suggests that products of chemical reactions following the oxidation of DPAS passivate the electrode. The electrode can be cleaned mechanically, or by pulsing into the background reduction of water (−1.4V vs SCE) for a few seconds, after which ECL can again be observed upon oxidation.

The oxidation of DPAS is complicated by following chemical reactions as evidenced by the lack of chemical reversibility shown in FIG. 3. This behavior, which persists at scan rates as high as 10 V/s, is probably due to the attack of DPAS$^+$ by water or OH- to form products. Although special care was taken to exclude traces of water from these solutions, it is likely that the five waters of hydration associated with DPAS provide a sufficient source for nucleophilic attack on DPAS$^+$. The addition of neutral alumina to these solutions in an attempt to remove water did not result in profound changes in the electrochemistry. Attempts to increase the ECL emission intensity via stabilization of DPAS$^+$ using surfactant or by the poly-sulfonation of DPA were not successful.

A calibration curve for ECL intensity vs. concentration over the sensitivity range for a Perkin-Elmer analyzer for DPAS at a concentration as low as $3.2\times10^{-8}$M is shown in FIG. 4. Under optimized conditions, Ru(bpy)$_3^{2+}$ can be detected at concentrations about 60 times more dilute at similar emission intensities. At higher concentrations of $5\times10^{-6}$M using the CCD camera (and correcting for the detector sensitivity) the Ru(bpy)$_3^{2+}$ emission is approx. 100 times more intense than the DPAS emission. Since the ECL emission for DPAS is expected to be more intense than for Ru(bpy)$_3^{2+}$ based upon fluorescence efficiencies ($\phi_F=0.87$ for DPAS and about 0.05 for Ru(bpy)$_3^{2+}$), lower ECL intensity for DPAS suggests the presence of competing chemical reactions (such as nucleophilic attack) that consume DPAS$^+$.

Figure 5:
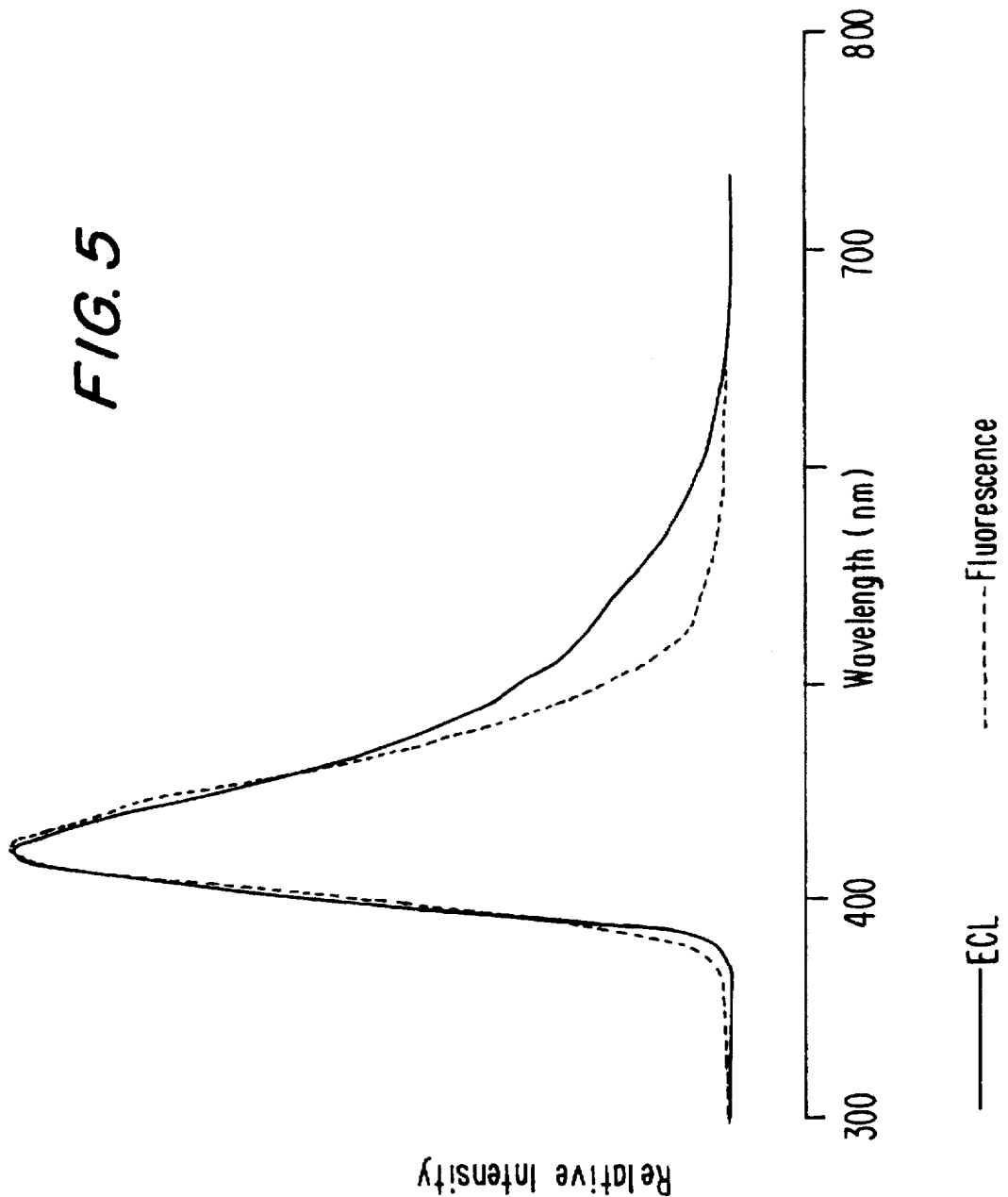
FIG. 5 shows fluorescence and ECL spectra for a solution of $1\times10^{-5}$M DPAS and 0.15M TPrA in pH 7.5 sodium phosphate buffer. The ECL emission was generated by repetitively pulsing a 6×9 mm Pt gauze (52 mesh) electrode from 0.0 V (vs SCE, 8 s.) to +1.2 V (2 s.) to −1.4 V (2s.) and back to 0.0 V. Light was generated on the positive pulse in this sequence (the negative pulse was for electrode cleaning purposes) and was integrated for 2 min. to produce the spectrum. Both peak intensities are at 430 nm.

FIG. 5 shows the ECL and fluorescence spectra of $1\times10^{-5}$M DPAS. The similarity between the fluorescence and ECL spectra suggests that the ECL emission is from DPAS*. The slight discrepancy between the spectra at long wavelengths may be due to emission from other products formed by competing chemical reactions during ECL.

EXAMPLE 2

The electrochemistry and ECL of the Ru(bpy)$_3^{2+}$/S$_2$O$_8^{2-}$ system in MeCN-water has been considered previously and the reductive CV of S$_2$O$_8^{2-}$ is shown in FIG. 6. Here, the irreversibility of the reaction is due to the process outlined in equation (13) above. Under these conditions, the onset of the background reduction of water (not shown) producing gaseous H$_2$ occurs at about −1.0 V.

In the present invention, cathodic reduction of DPAS occurs in the presence of S$_2$O$_8^{2-}$ as the coreactant and produces ECL. The reduction of DPAS in MeCN is shown in FIG. 7 and the reversibility of this couple (DPAS$^{0/-}$) compared to the oxidation of DPAS shown in FIG. 3 indicates that DPAS$^-$ is significantly more stable in MeCN than DPAS+. The small prewave in FIG. 7 appears to be due to adsorbed DPAS since the current for this wave increases linearly with scan rate ($\upsilon$) whereas that for the more negative couple increases with $\upsilon^{1/2}$ over a range of 0.1 to 10 V/s. Because this reduction occurs well into the background reduction of water, no cathodic current above background is evident in MeCN-water (1:1 by volume) solutions. However, if the potential is scanned into the background reduction of water in the presence of S$_2$O$_8^{2-}$, a bright blue emission is observed at a potential corresponding to the reduction of DPAS (after making the approximate conversion from ferrocene to SCE potentials) as shown in FIG. 8. No emission is observed in the absence of either S$_2$O$_8^{2-}$ or DPAS. This result is consistent with previous results with the Ru(bpy)$_3^{2+}$/S$_2$O$_8^{2-}$ system in which no emission is seen until the potential is scanned sufficiently negative to reduce Ru(bpy)$_3^{2+}$ and allow generation of the excited state via the sequence of reactions shown in equations (12)–(15) above. This scheme can be modified to describe the ECL reaction for DPAS by substituting DPAS$^{+/0/-}$ respectively for Ru(bpy)$_3^{3+/2+/+}$.

As shown in FIG. 9, the blue ECL spectrum for the DPAS emission matches the fluorescence spectrum and also matches the ECL and fluorescence spectra for the oxidative-reduction of DPAS with TPrA shown in FIG. 5. The smaller emission contribution from side products in FIG. 9, confirms better stability of DPAS$^-$, even during the background reduction. In considering the energetics of an ECL system one notes the standard potentials of the relevant half-reactions (yielding the free energy of the electron transfer reaction) and the energy of the emitting state. For the oxidation of DPAS and TPrA these are:

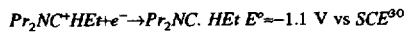

The enthalpy of the electron transfer reaction between DPAS$^+$. and Pr$_2$NC.HEt, correcting for an entropy of about 0.1 eV, is −2.3 eV, well below that needed to produce singlet DPAS*, so that this would be classified as an "energy-deficient" reaction. As with other reactions of this type, excited singlets probably form via triplet-triplet annihilation (a T-route). Although the oxidative DPAS/oxalate system would be "energy-sufficient", no emission was observed for runs with oxalate as the coreactant.

The reductive path energetics corresponds to the half reactions:

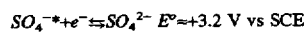

In this case the electron transfer reaction between DPAS$^-$* and SO$_4^-$* is sufficient to produce singlet DPAS* directly (an S-route). The emission intensity for $1\times10^{-5}$M DPAS is about the same for the DPAS/TPrA oxidation as it is for the DPAS/S$_2$O$_8^{2-}$ reduction.

EXAMPLES 3 AND 4

1-THCOOH and 2-THCOOH were synthesized following the procedures of Gilman and Swayampati described in Gilman, H.; Swayampati, D. R. *J. Am. Chem. Soc.* 1957, 79, 208. with the exception that 1.6M n-butyllithium in hexane was substituted for their ethereal solutions of n-butyllithium.

Figure 10A:
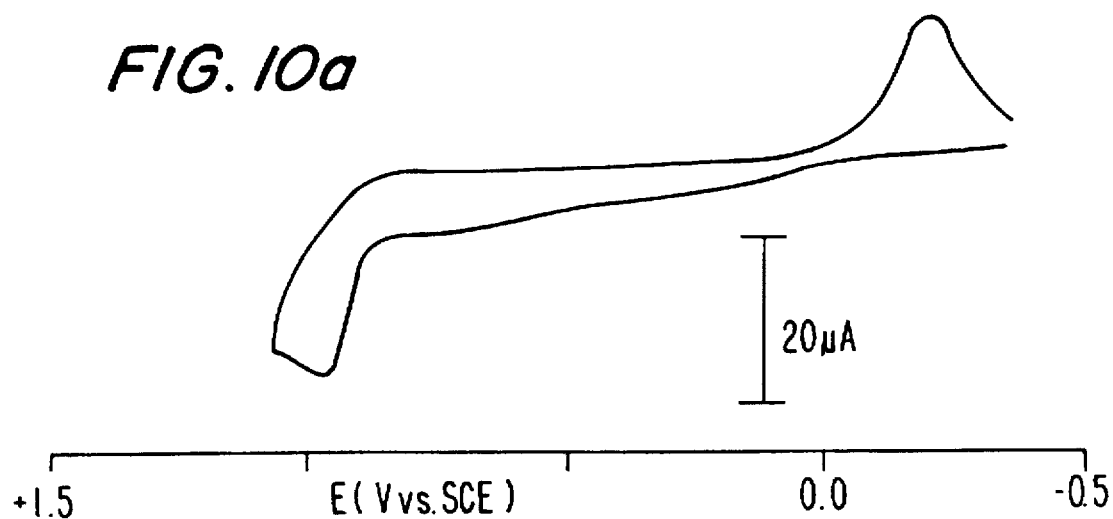
FIGS. 10a–10c show (a) Cyclic voltammogram of 2.0 mM 2-THCOOH in pH 8.5 sodium phosphate buffer at a 1.5 mm dia. Pt electrode at scan rate of 200 mV/s; (b) Cyclic voltammogram of 1.4 mM 2-THCOOH under the same conditions as (a) except that the scan cycled from +0.15 V instead of from −0.35 V; and (c) Cyclic voltammogram of 2.0 mM 2-THCOOH at a 1.5 mm dia. Pt electrode in MeCN, 0.1M $TBABF_4$ at a scan rate of 200 mV/s. Aqueous scans (a) and (b) are referenced to SCE. Non-aqueous scan (c) is referenced to ferrocene.
Figure 10B:
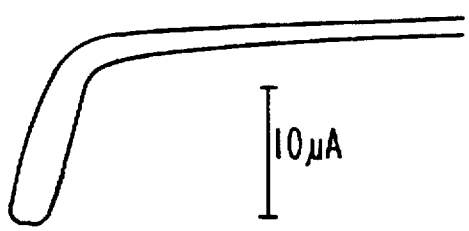
Figure 10C:
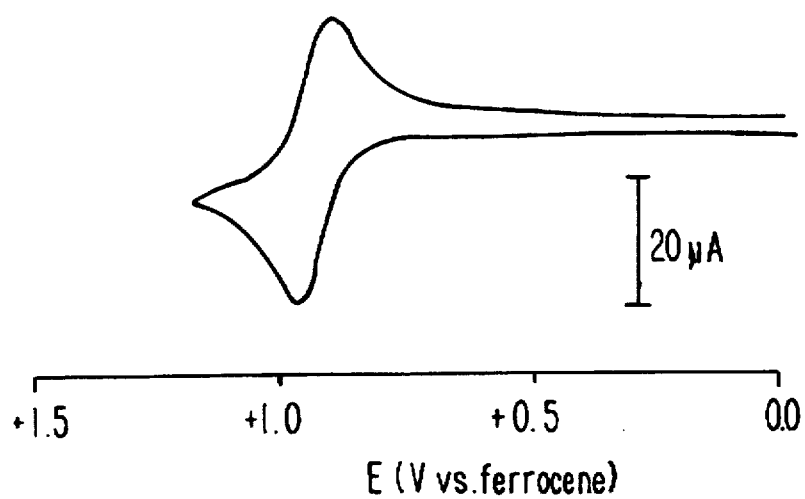

The oxidation of 2-THCOOH in aqueous solution occurs near +1.0 V as shown in FIG. 10a. The broad anodic process between 0.0 V and +0.5 V as well as the more prominent cathodic process at −0.2 V are characteristic of oxide formation and reduction at a Pt electrode in aqueous solution at this pH and appear in scans in the absence of 2-THCOOH. These processes can be eliminated if the potential is cycled no further negative than +0.15V as shown in FIG. 10b. The chemical irreversibility shown in FIGS. 10a and 10b (and observed in similar scannings up to 50 V/s) indicates the instability of oxidized 2-THCOOH in aqueous solution and its rapid conversion to some product. In contrast to this, similar runs in dry MeCN(FIG. 10c) show the oxidized product to be stable. This shows that the decomposition of the oxidized acid is due to reaction with water as opposed to other possibilities such as decarboxylation with the loss of CO$_2$.

The oxidation of thianthrene (TH)in MeCN produces a stable radical cation described in Kexzthelyi, C. P.; Tachikawa, H.; Bard, A. J. *J. Am. Chem. Soc.* 1972, 94, 1522, hence the oxidation of THCOOH probably proceeds in a similar way:

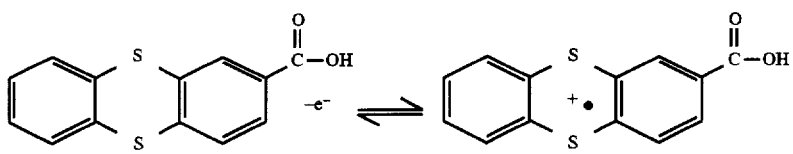

Nucleophiles like $H_2O$ and $OH^-$ are known to attack $TH^+$, at the sulfur, and this is very likely in aqueous solutions, leading, for example to the sulfoxide:

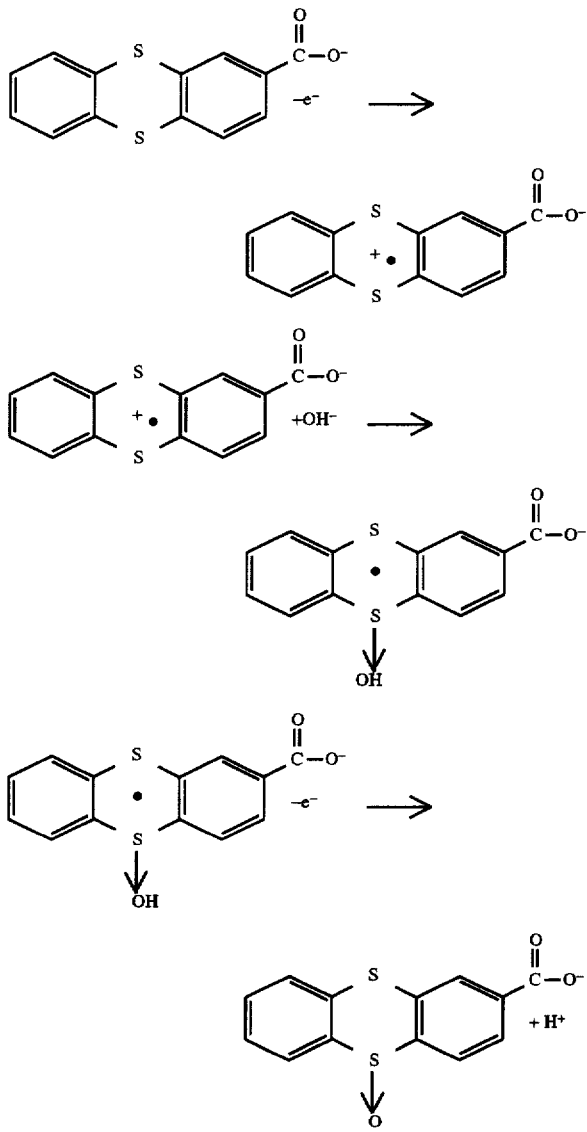

Figure 11:
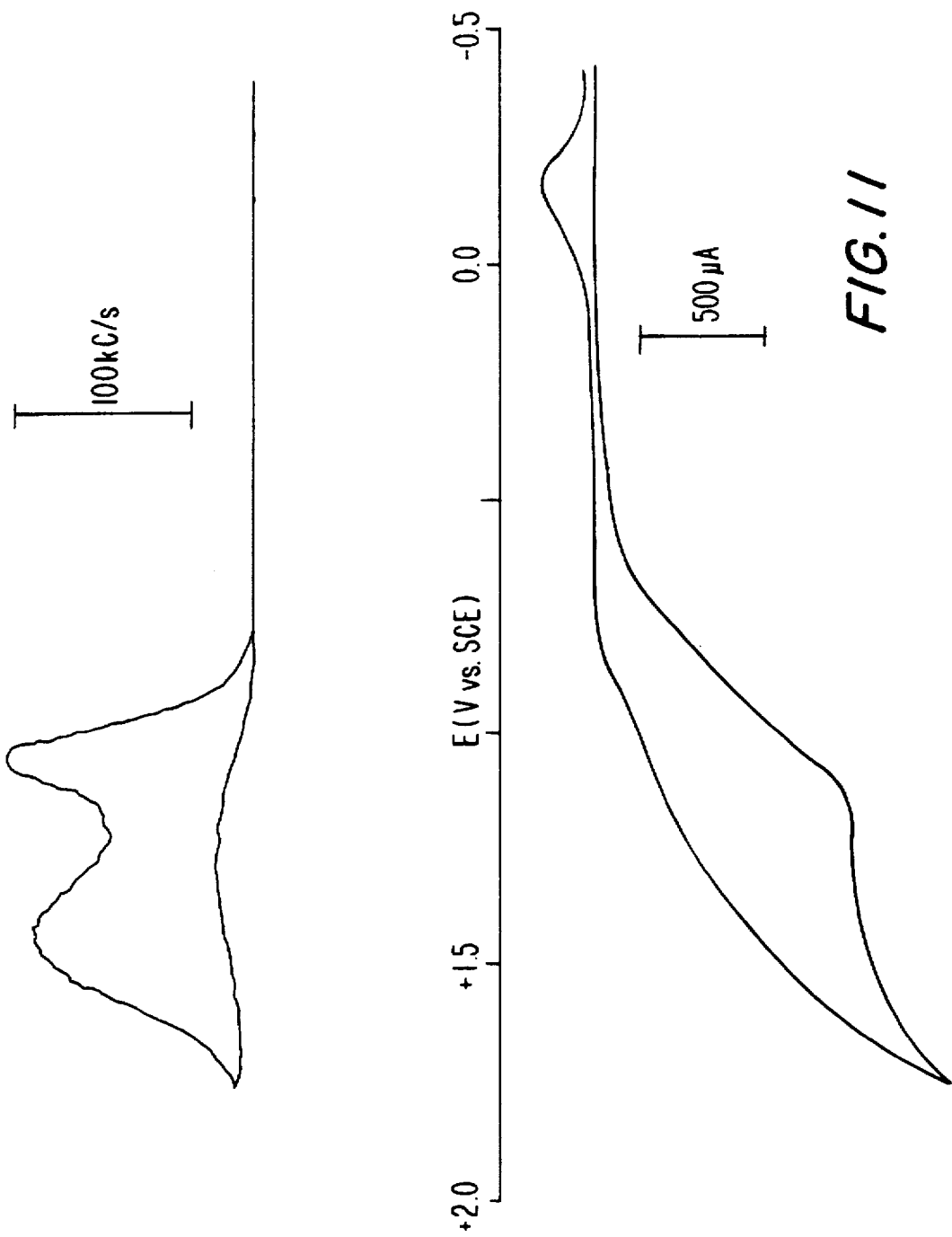
FIGS. 11a–11b show (a) cyclic voltammogram (bottom) and (b) simultaneous emission of 5.2 mM 2-THCOOH and 0.15M TPrA in pH 7.5 sodium phosphate buffer at a 6 mm dia. Pt electrode at a scan rate of 100 mV/s.
Figure 12:
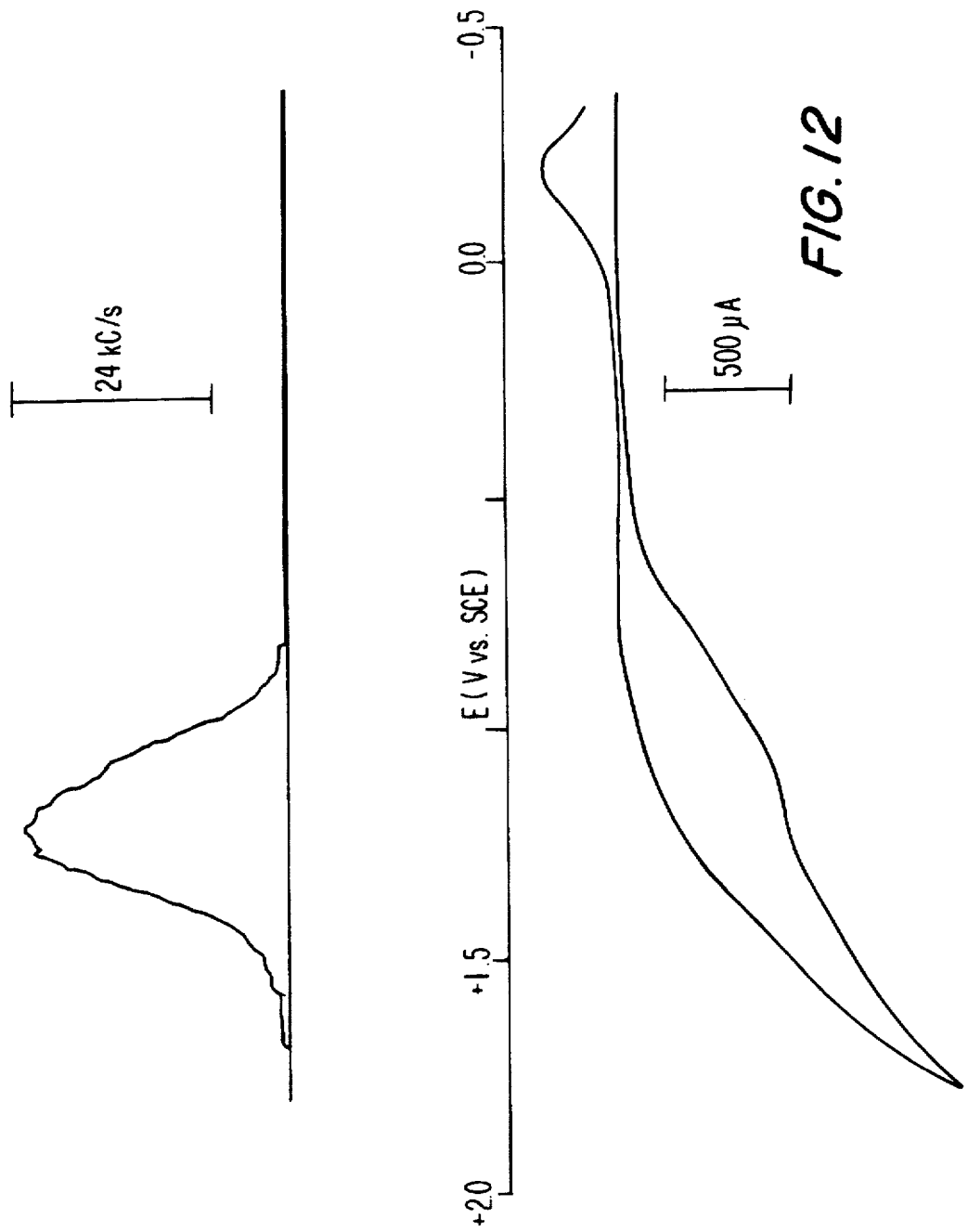
FIGS. 12a–12b show (a) cyclic voltammogram and (b) simultaneous emission of 0.26 mM 2-THCOOH and 0.15M TPrA under the same conditions as FIG. 11.

Both 1-THCOOH and 2-THCOOH produce ECL emission when oxidized in aqueous sodium phosphate buffer solution in the presence of TPrA as a coreactant as shown in FIGS. 11 and 12 for 2-THCOOH. (The behavior of 1-THCOOH is similar except that the peak emission intensity is 6–7 times less intense than that of 2-THCOOH). In the absence of TPrA or the acid, no emission is observed. Although the anodic current is dominated by the oxidation of the deprotonated acid, the electrochemistry is complicated by the coincidence of this process with both the onset of the broad, irreversible oxidation wave for TPrA (FIG. 2c) and the background oxidation of water (FIG. 1). The two distinct emission peaks as a function of potential in FIG. 11 suggest contributions from two different electrode processes. The first peak is believed due to reactions associated with the homogeneous oxidation of TPrA following equation (6a) above (with 2-TH$^+$COO$^-$ replacing Ru(bpy)$_3^{3+}$) and the second peak results from the direct heterogeneous oxidation of TPrA at the electrode following equation (6). This hypothesis is supported by the results of FIG. 12 recorded at a lower 2-THCOOH concentration where the second-order reaction of (6a) will be slower and less important. Under the conditions of FIG. 12, the emission from the homogeneous process appears as a small shoulder in the dominant emission brought on by the heterogeneous oxidation of TPrA. The negative shift in the second emission peak can be rationalized on the basis of a larger concentration of TPrA at the electrode at more negative potentials due to the inactivity of the TPrA-depleting homogeneous oxidation reaction (6a).

Figure 13:
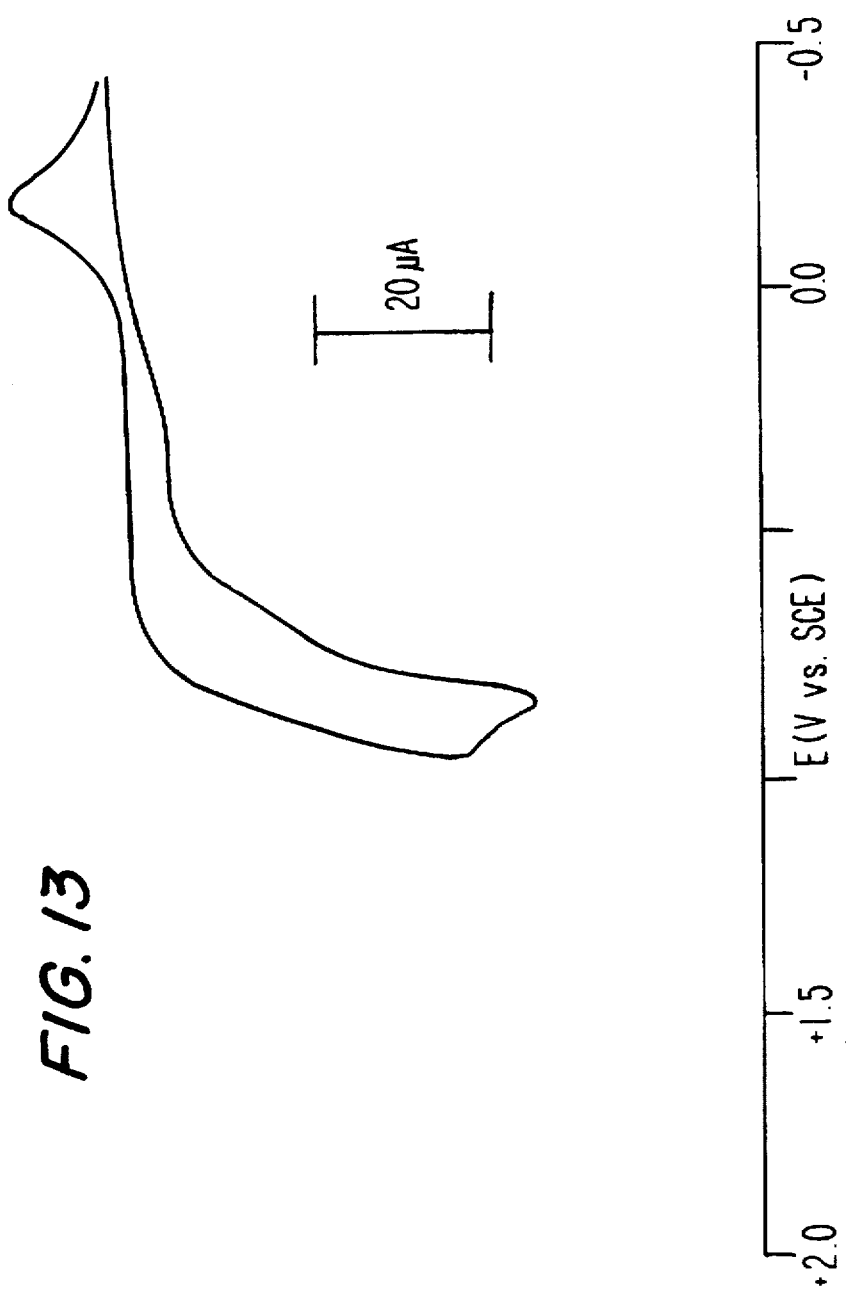

When 2-THCOOH is oxidized in the presence of TPrA, the anodic current nearly doubles compared to that at the same 2-THCOOH concentration in the absence of TPrA, (compare FIGS. 10a and 13). This is consistent with the catalytic regeneration of the THCOOH (or some product) via its homogeneous reduction by TPrA or an intermediate (following the analogy to (6a) or (8)–(9) for this system) and supports the hypothesis that the first emission peak in FIG. 11 is due to the generation of coreactant precursors via the homogeneous oxidation of TPrA.

Figure 14:
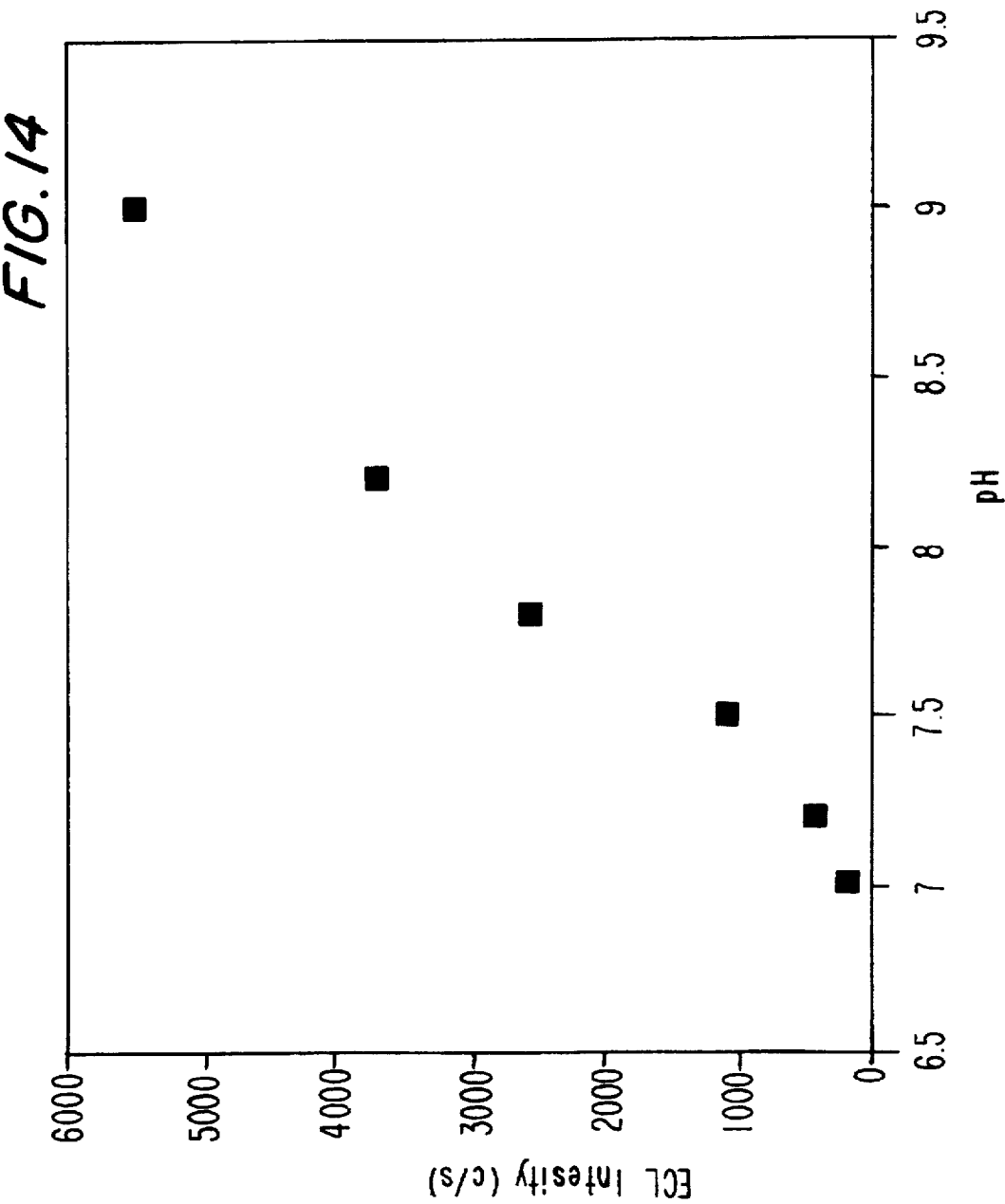
FIG. 14 shows peak ECL intensity vs. pH for $1\times10^{-5}$M 2-THCOOH, 0.15M TPrA in sodium phosphate buffer.
Figure 15:
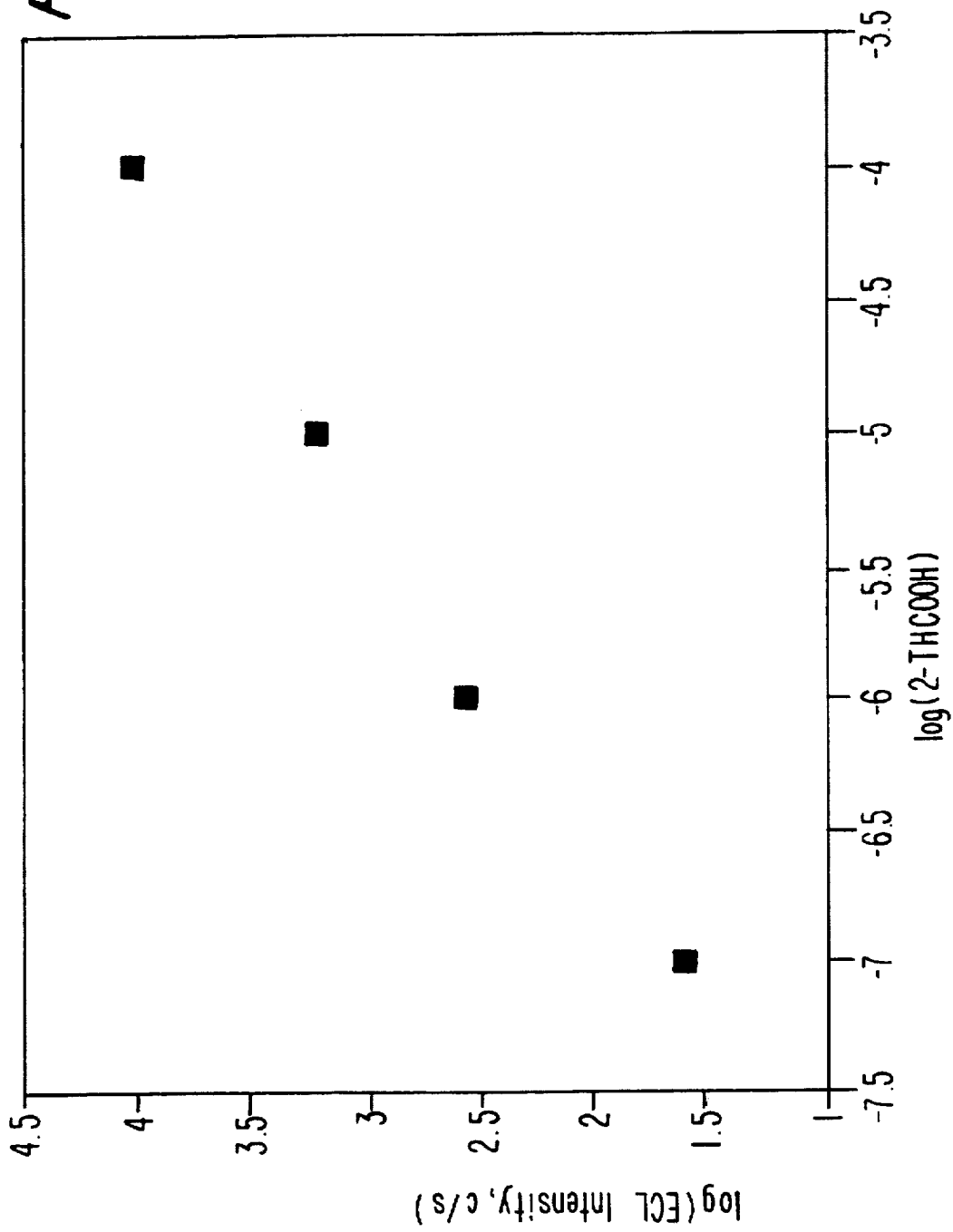
FIG. 15 shows a log-log plot of peak ECL intensity vs. 2-THCOOH concentration in pH 7.5 sodium phosphate buffer containing 0.15M TPrA.

In FIG. 14, the peak emission intensity for $1 \times 10^{-5}$M 2-THCOOH increases with pH. The difference between the trend seen here and that for the Ru(bpy)$_3^{2+}$/TPrA system, which shows a peak near pH 7.5, suggests that $H^+$ is involved not only in decomposition reactions of TPrA but also in reactions associated with the emission from a product of 2-THCOOH. The peak emission intensity for 2-THCOOH varies linearly with concentration over 4 orders of magnitude at pH 7.5, as shown in FIG. 15.

Figure 16A:
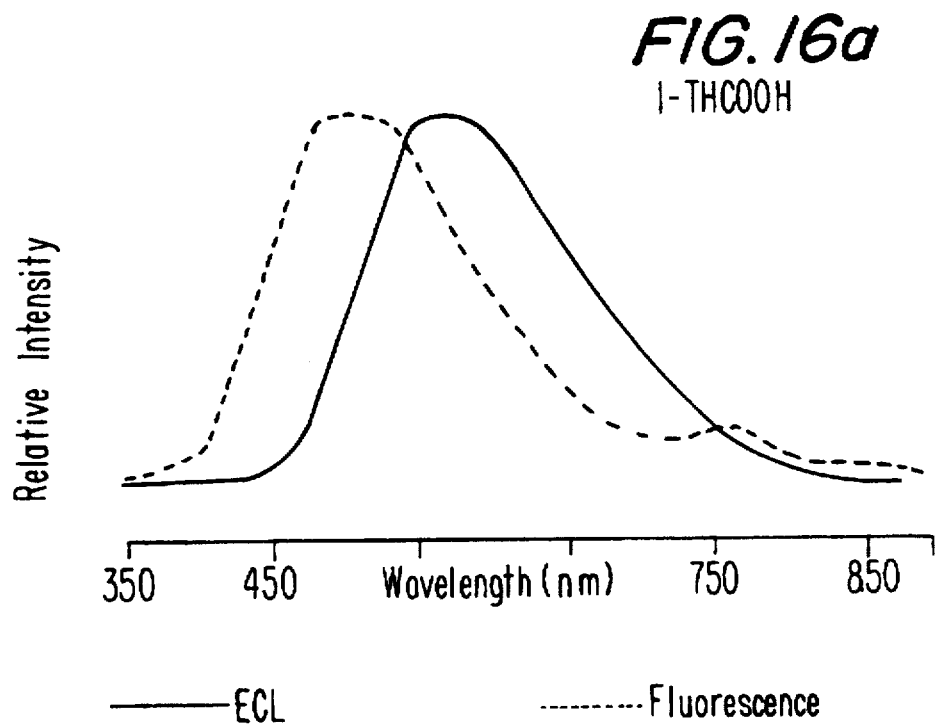
FIG. 16a–16b show the fluorescence and ECL spectra of 9.1 mM 1-THCOOH (a) and 20 mM 2-THCOOH (b) taken in pH 8.5 sodium phosphate buffer containing 0.15M TPrA. ECL emissions were generated by alternately pulsing a 6×9 mm Pt gauze (52 mesh) electrode between +1.4 V (0.5 s.) and −0.5V(2s.) vs SCE for a duration of 40 min. for 1-THCOOH and 20 min. for 2-THCOOH with a stirred solution. The peak fluorescence intensity is at 480 nm for 2-THCOOH and 505 nm for 1-THCOOH. The peak ECL intensities are at 570 nm for both isomers. The intensities have been scaled for comparison purposes. At equal THCOOH concentrations (20 mM) and acquisition times, the intensity of the 2-THCOOH emissions are approximately 6–7 times those of 1-THCOOH.
Figure 16B:
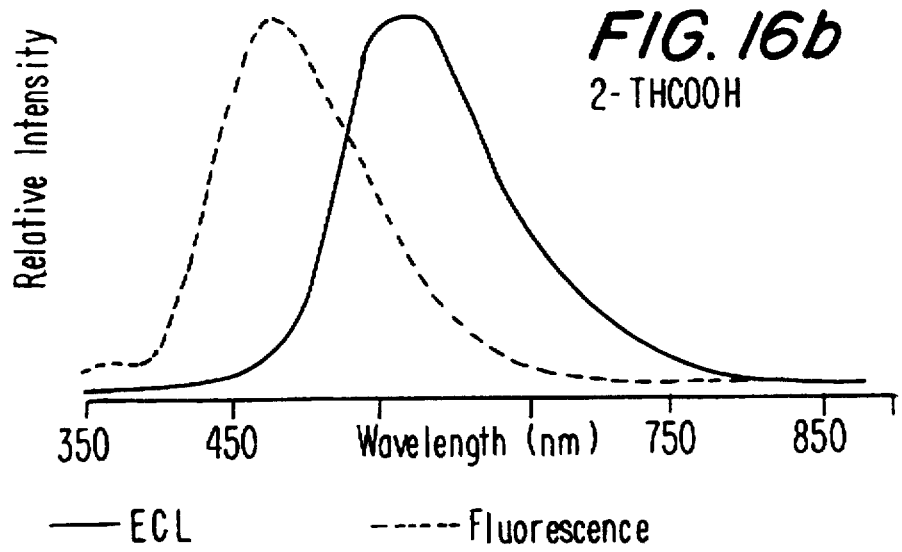

The fluorescence and ECL spectra of 1-THCOOH and 2-THCOOH are shown in FIG. 16. The fluorescence maxima for 1-THCOOH and 2-THCOOH are at 505 nm and 480 nm respectively. For comparison, the emission maximum for thianthrene fluorescence in MeCN is at 434 nm. The ECL maxima for each acid is at 570 nm showing a strong shift toward longer wavelength compared to the respective fluorescence spectra. Under these optimized conditions, the 2-THCOOH emission is just visible to the dark-adapted eye.

The differences between the fluorescence and ECL spectra for the THCOOH acids suggests that at least part of the ECL emission is from some species other than an excited state of the intact acid. One possibility is that the acid decarboxylates upon oxidation but this is unlikely for several reasons: 1) if decarboxylation occurred one would expect the emission to be characteristic of either TH or THCOOH which it is not, 2) if TH were produced via decarboxylation, it would precipitate on the electrode because of its low solubility in aqueous solutions and no evidence of this is observed. 3) under non-aqueous conditions (dry MeCN), the oxidized acid is stable on the voltammetric time scale as evidenced by the return wave shown in FIG. 10c. Consideraction of electrochemical studies demonstrating nucleophilic attack by water at the sulfur position for TH cation radical suggests that similar reactions may occur with the THCOOH acids. Also a parallels exists between the THCOOH ECL results and those observed for anthracene. In the case of anthracene, a similar red-shifted ECL emission is observed upon generation of the radical cation and is attributed to emission from anthranol (the enol form of the ketone anthrone) formed from the reaction of anthracene radical cation with traces of water in the MeCN solvent. Presumably, the emission observed from 1- and 2-THCOOH occurs from similar intermediates formed by the reaction of the oxidized acid with water. The ECL spectrum for both acids has the same peak wavelength whereas the peaks are distinct for the fluorescence spectra. The energy of the emitting intermediate is more strongly affected by the added nucleophile than by the position of the carboxylic acid function.

EXAMPLE 5

Figure 17A:
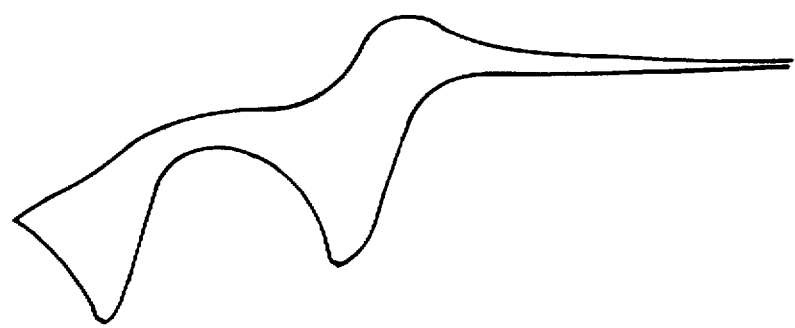
FIGS. 17a–17b show (a) the cyclic voltammogram of 0.98 mM CPZ in 0.01M HCl, 0.2M NaCl at a 6 mm dia. HOPG electrode at a scan rate of 50 mV/s and (b) the cyclic voltammogram for the same system and conditions as (a) with scan reversal after the first oxidation.
Figure 17B:
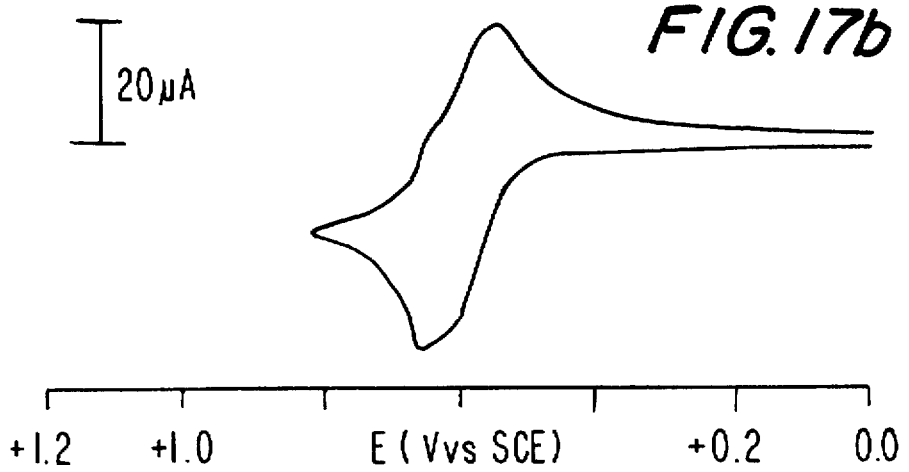

Cyclic voltammograms for the oxidation of chlorpromazine (FIG. 17) show the oxidation to proceed as two discrete processes. The first of these is quasi-reversible and the second is irreversible. The abnormally sharp peak on the first anodic wave seen in FIGS. 17a–17b has been attributed to adsorption of CPZ. Likewise, the shoulder on the cathodic return wave in FIG. 17b is an adsorption process. When the scan is reversed after the first oxidation as shown in FIG. 17b, the increased reversibility (compared to FIG. 17a) suggests that a product from the second oxidation reacts with the oxidized form of CPZ.

Figure 18:
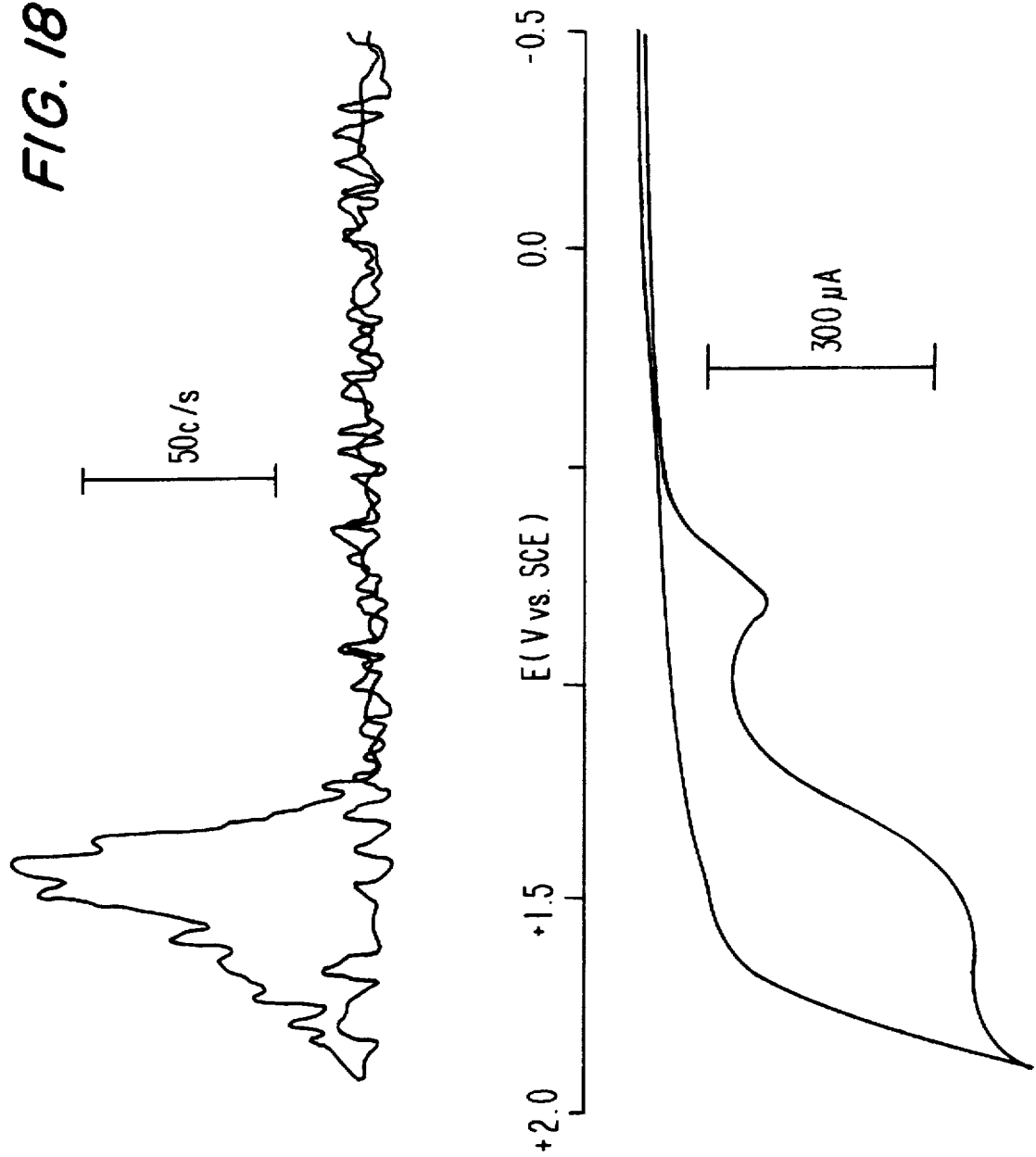
FIGS. 18a–18b show (a) the cyclic voltammogram and (b) simultaneous emission for 1.0 mM CPZ taken at a 6 mm dia. HOPG electrode in pH 7.5 sodium phosphate buffer at a scan rate of 200 mV/s.

Oxidizing CPZ at higher pH in sodium phosphate buffer solution, alters the electrochemistry as shown in FIG. 18a. The first oxidation is now irreversible and the electrochemistry is in general more complex than that of FIG. 17 as evidenced by a shoulder on the first oxidation wave, increased current, and a broadening of the second wave. As with the TPrA oxidation, analysis of the second oxidation process is complicated by its coincidence with the background oxidation of water. However, (in the absence of an added coreactant) as shown in FIG. 18, ECL emission is unexpectedly obtained. Verifications of the ECL spectrum for this process for comparison to the photoluminescence spectrum were hampered by low emission intensities and electrode fouling. In addition, attempts to determine the wavelength of the peak emission using interference filters for specific, narrow wavelength ranges between 450 and 600 nm were unsuccessful. No emission is observed under the conditions of FIG. 17 (with or without 50 mM TPrA added) where the electrochemistry is less complex and electrode fouling does not occur.

Earlier mechanistic work by McCreery has shown that mono-oxidized forms of CPZ are converted to sulfoxides in aqueous solution via nucleophilic attack by water at the sulfur position. Thus, the first oxidation of CPZ is associated with the tricyclic ring system and the second oxidation involves the tertiary amine on the side chain (analogous to the oxidation of THCOOH and TPrA). Presumably, the amine then undergoes reactions similar to those seen with TPrA in equation (6)–(7) above, to produce a strong reducing agent that reacts with the ring system to generate a luminescent excited state. This "self-annihilation" ECL process probably proceeds as shown in equations (5)–(8), where the tricyclic portion of CPZ replaces Ru(bpy)$_3^{2+}$ and is covalently bonded to the coreactant X (the tertiary amine on the side chain). The self-annihilation could proceed via an intramolecular or an intermolecular process. The CPZ emission is from a product formed by the reaction of oxidized CPZ with water. For 0.11 mM CPZ in pH 7.5 sodium phosphate buffer, a peak emission intensity of 80 c/s above background, was recorded. For 1.1 mM CPZ, the peak intensity was 850 c/s.

EXAMPLE 6

Figure 19:
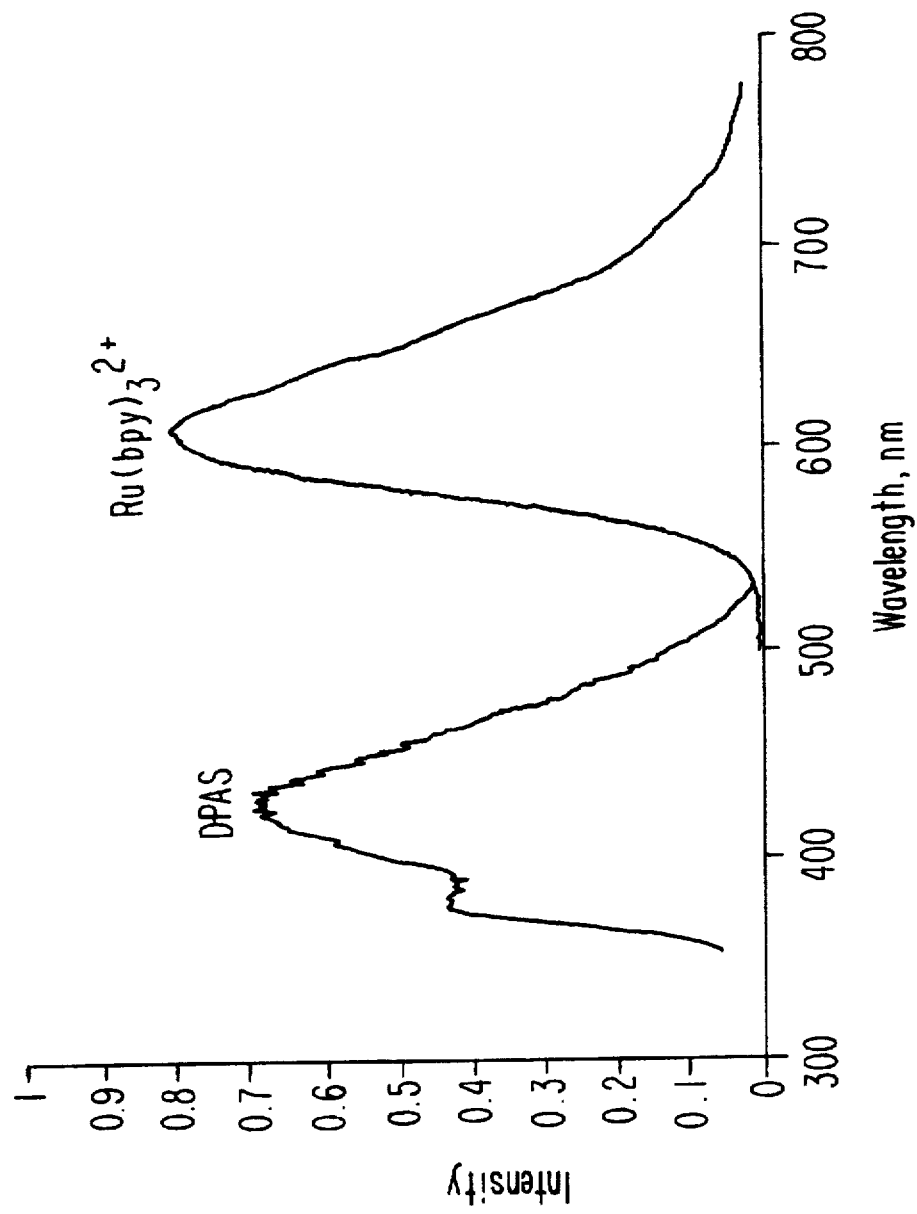
FIG. 19 shows the emission spectra of DPAS and Ru(bpy)$_3^{2+}$.

In order to eliminate variances in ECL detection measurements of a sample, an internal standard technique is used. In the internal standard method, a fixed quantity of a reference is added to the sample. Upon excitation, the ECL intensity of the sample and reference are measured simultaneously. The ratio of ECL intensities will be unaffected by normal variations in the measurement technique. The internal standard is useful to correct for matrix effects, temperature fluctuations, excitation voltage variances, etc. The internal standard is only valid if the matrix effects the reference signal and sample in exactly the same way. Use of this evaluation method is limited to instrument designs and ECL methods capable of determining two luminophore emissions. Selection of an appropriate reference luminophore is critical to the performance of the technique. The choice of reference luminophore depends on the relative positions of the emission spectra of the sample and reference. In the example presented, DPAS is an ideal candidate for a reference luminophore because its emission is well separated from the sample luminophore Ru(bpy)$_3^{2+}$. FIG. 19 shows the emission spectra. The 430 nM wavelength centered emission of DPAS is well separated from the 620 nM wavelength centered emission of Ru(bpy)$_3^{2+}$.

Figure 20:
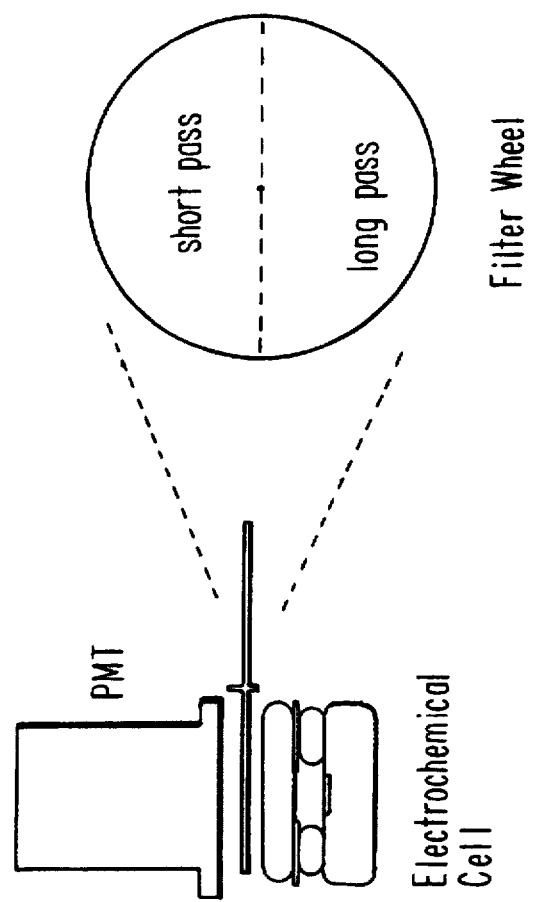
FIG. 20 shows a device for measuring two ECL emissions.

The two ECL emissions can be resolved by wavelength with the use of optical filters. The optical arrangement is shown in FIG. 20. A wheel is constructed of two optical filters placed between the electrochemical cell and PMT. The wheel has a long pass filter for observation of Ru(bpy)$_3^{2+}$ emission and a short pass filter for observation of DPAS emission. The rotation of the optical wheel is synchronized to the excitation voltage. During an excitation two ECL emissions are observed. The excitation voltage ramp is divided into two periods; FIGS. 21a–21c. During the first period, the optical wheel is positioned with the long pass filter above the electrode. The emission from the sample is measured. Emission from the reference is filtered. During the second period, the optical wheel is positioned with the short pass filter above the electrode. The emission from the reference is measured, and the sample is filtered. The sample signal is obtained by integrating the area for the ECL emission under the first period. The reference sample is obtained from the area for the second period. The internal standardization is made by ratioing the sample signal to the reference signal. Any variances unrelated to concentration changes are observed in both the sample and reference. The ratio signal is then used to measure the concentration of the sample.

EXAMPLE 7

ECL detection methodology is suitable for quantification of DNA hybridization assays. The ECL intensity is proportional to the concentration of the particular DNA analyte of interest. The variances in the amplification of the DNA prior to ECL detection may also be eliminated using an internal standard.

While particular embodiments of the present invention have been illustrated and described herein, the present invention should not be limited to such illustrations and description. It should be apparent that changes and modifications may be incorporated and embodied as part of the present invention within the scope of the following claims.

We claim:

1. A composition, comprising:
   (a) a substituted polycyclic molecule selected from the group consisting of 1-thianthrenecarboxylic acid, 2-thianthrenecarboxylic acid, and chlorpromazine; and corresponding salts or derivatives thereof; and
   (b) a coreactant, wherein said molecule and said coreactant upon exposure to electrochemical energy interact to produce electrochemiluminescence at an emission wavelength distinct from that of Ru(bpy)$_3^{+2}$.

2. The composition of claim 1, wherein: said molecule is selected from the group consisting of 1-thianthrenecarboxylic acid, and 2-thianthrenecarboxylic acid.

3. The composition of claim 2, wherein:
   (a) said coreactant is tri-n-propylamine or peroxydisulfate.

4. The composition of claim 1, wherein: said molecule is chlorpromazine.

5. The composition of claim 4, wherein:
   (a) relative to said chlorpromazine, said coreactant is a covalently-bonded moiety thereof.

6. The composition of claim 1, wherein said molecule is in a solvent comprising water.

7. The composition of claim 6, wherein:
   (a) said solvent comprises a mixture of water and acetonitrile.

8. The composition of claim 6, wherein:
   (a) said solvent contains at least one supporting electrolyte.

9. The composition of claim 8, wherein:
   (a) said solvent contains a mixture of at least two different supporting electrolytes.

10. The composition of claim 7, wherein:
    (a) said solvent contains tetrabutylammonium tetrafluoroborate as a supporting electrolyte.

11. A process for performing an assay, comprising:
    (a) exposing a solution containing a first electrochemiluminescent label comprising a substituted polycyclic molecule selected from the group consisting of 1-thianthrenecarboxylic acid 2-thianthrenecarboxylic acid, and chlorpromazine; and corresponding salts or derivatives thereof having a binding partner of a first analyte of interest attached thereto wherein said solution is suspected of containing a first analyte of interest, to electrochemical energy and thereby producing electrochemiluminescence; and
    (b) detecting the produced electrochemiluminescence and thereby determining the presence or absence of the first analyte.

12. The process of claim 11, wherein:
    (a) said detecting quantitatively determines the amount of the first analyte.

13. The process of claim 12, wherein:
    (a) said detecting involves correlating the produced electrochemiluminescence with a calibration standard.

14. The process of claim 11, wherein, a coreactant is utilized for producing the electrochemiluminescence of the molecule.

15. The process of claim 14, wherein:
    (a) the molecule is selected from the group consisting of 1-thianthrenecarboxylic acid and 2-thianthrenecarboxylic acid; and
    (b) the coreactant is tri-n-propylamine or peroxydisulfate.

16. The process of claim 14, wherein:
    (a) the molecule is chlorpromazine; and,
    (b) relative to said chlorpromazine, the coreactant is a covalently-bonded moiety thereof.

17. The process of claim 11, further comprising:
    (a) introducing a second electrochemiluminescent label comprising Ru(bpy)$_3^{2+}$ having a binding partner of a second analyte of interest attached thereto into the solution prior to said exposing of the solution to electrochemical energy; and
    (b) wherein said detecting of electrochemiluminescence is performed at different wave lengths for each electrochemiluminescent label thereby determining the presence or the absence of a plurality of analytes.

18. A compound, comprising:
    (a) a substituted polycyclic molecule selected from the group consisting essentially of 1-thianthrenecarboxylic acid and 2-thianthrenecarboxylic acid; and corresponding salts or derivatives thereof; wherein said molecule electrochemiluminesces at an emission wavelength distinct from that of Ru(bpy)$_3^{+2}$ upon exposure to electrochemical energy.

19. A composition consisting essentially of:
    (a) a substituted polycyclic molecule selected from the group consisting of 1-thianthrenecarboxylic acid, 2-thianthrenecarboxylic acid, and chlorpromazine, and corresponding salts or derivatives thereof; and
    (b) tri-n-propylamine coreactant, wherein said molecule and said amine upon exposure to electrochemical energy interact to produce electrochemiluminescence at an emission wavelength distinct from that of Ru(bpy)$_3^{+2}$.

20. A process for performing an assay, comprising:
    (a) exposing a solution containing a composition consisting essentially of a first electrochemiluminescent label comprising a substituted polycyclic molecule selected from the group consisting of 1-thianthrenecarboxylic acid, 2-thianthrenecarboxylic acid, and chlorpromazine, and corresponding salts or derivatives thereof said molecule having a binding partner of a first analyte of interest attached thereto and a tri-n-propylamine coreactant, wherein said solution is suspected of containing a first analyte of interest, to electrochemical energy and thereby producing electrochemiluminescence; and
    (b) detecting the produced electrochemiluminescence and thereby determining the presence or absence of the first analyte.

21. The process of claim 20, further comprising:
    (a) introducing a second electrochemiluminescent label comprising Ru(bpy)$_3^{2+}$ having a binding partner of a second analyte of interest attached thereto into the solution prior to said exposing of the solution to electrochemical energy; and
    (b) wherein said detecting of electrochemiluminescence is performed at different wavelengths for each electrochemiluminescent label and determining the presence of the absence of a plurality of analytes.

* * * * *